(12) United States Patent
Zhao et al.

(10) Patent No.: US 11,957,773 B2
(45) Date of Patent: *Apr. 16, 2024

(54) HAIR CONDITIONER COMPOSITIONS CONTAINING BEHENAMIDOPROPYL DIMETHYLAMINE

(71) Applicant: The Procter & Gamble Company, Cincinnati, OH (US)

(72) Inventors: Jean Jianqun Zhao, Cincinnati, OH (US); Lauren Elizabeth Ballhaus, Williamsburg, OH (US); Heather Lynn Focht, Lebanon, OH (US); David Joseph Kaufman, Fairfield, OH (US); Christina Marie McQueen, Middletown, OH (US); Deborah Mulligan, Montgomery, OH (US); Lina Aurora Witte, Monroe, OH (US)

(73) Assignee: The Procter & Gamble Company, Cincinnati, OH (US)

(*) Notice: Subject to any disclaimer, the term of this patent is extended or adjusted under 35 U.S.C. 154(b) by 240 days.

This patent is subject to a terminal disclaimer.

(21) Appl. No.: 17/108,081

(22) Filed: Dec. 1, 2020

(65) Prior Publication Data

US 2021/0161784 A1 Jun. 3, 2021

Related U.S. Application Data

(60) Provisional application No. 62/942,209, filed on Dec. 2, 2019, provisional application No. 62/942,208, filed on Dec. 1, 2019.

(51) Int. Cl.
| | |
|---|---|
| *A61K 8/34* | (2006.01) |
| *A61K 8/04* | (2006.01) |
| *A61K 8/19* | (2006.01) |
| *A61K 8/20* | (2006.01) |
| *A61K 8/36* | (2006.01) |
| *A61K 8/368* | (2006.01) |
| *A61K 8/37* | (2006.01) |
| *A61K 8/41* | (2006.01) |
| *A61K 8/42* | (2006.01) |
| *A61Q 5/12* | (2006.01) |

(52) U.S. Cl.
CPC .............. *A61K 8/345* (2013.01); *A61K 8/042* (2013.01); *A61K 8/19* (2013.01); *A61K 8/20* (2013.01); *A61K 8/342* (2013.01); *A61K 8/36* (2013.01); *A61K 8/368* (2013.01); *A61K 8/375* (2013.01); *A61K 8/416* (2013.01); *A61K 8/42* (2013.01); *A61Q 5/12* (2013.01); *A61K 2800/30* (2013.01); *A61K 2800/34* (2013.01); *A61K 2800/524* (2013.01)

(58) Field of Classification Search
CPC .... A61K 2800/524; A61K 8/042; A61Q 5/12; A61Q 5/02
See application file for complete search history.

(56) References Cited

U.S. PATENT DOCUMENTS

| | | |
|---|---|---|
| 2,356,168 A | 8/1944 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,613,185 A | 10/1952 | Marshall |
| 2,658,072 A | 11/1953 | Kosmin |
| 2,694,668 A | 11/1954 | Fricke |
| 2,809,971 A | 10/1957 | Bernstein et al. |
| 3,152,046 A | 10/1964 | Kapral |
| 3,236,733 A | 2/1966 | Karsten et al. |
| 3,321,425 A | 5/1967 | Blau et al. |
| 3,332,880 A | 7/1967 | Kessler et al. |
| 3,426,440 A | 2/1969 | Shen et al. |
| 3,463,308 A | 8/1969 | Deneke |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |

(Continued)

FOREIGN PATENT DOCUMENTS

| | | |
|---|---|---|
| CN | 1138091 | 12/1996 |
| CN | 1219388 | 6/1999 |

(Continued)

OTHER PUBLICATIONS

Final Report. https://journals.sagepub.com/doi/pdf/10.1080/10915810490499064. p. 55-94. Published: 2004.*
Lexgard Natural. https://www.asharrison.com.au/wp-content/uploads/2015/11/Lexgard%C2%AE-Natural.pdf. Copyright: 2013.*
PCT Search Report and Written Opinion for PCT/US2020/062654 dated Mar. 17, 2021.
All Office Actions, U.S. Appl. No. 16/953,975.
All Office Actions, U.S. Appl. No. 17/108,090.
All Office Actions, U.S. Appl. No. 17/209,292.

(Continued)

*Primary Examiner* — Robert T. Crow
*Assistant Examiner* — John P Nguyen
(74) *Attorney, Agent, or Firm* — John G. Powell; Kathleen Y. Carter

(57) ABSTRACT

A hair conditioner composition containing an aqueous carrier, from about 2.5 wt % to about 6.7 wt % of a behenamidopropyl dimethylamine, from about 3 wt % to about 8 wt % of a fatty alcohol; and less than 1.5 wt % of a salt. The molar ratio of behenamidopropyl dimethylamine to fatty alcohol can be from about 7:50 to about 4:5. The conditioner composition can have a uniform gel network. The composition can have d-spacing of less than 32 nm, as measured according to the d-spacing (Lβ-basal spacing) of Lamella Gel Network Test Method.

19 Claims, 3 Drawing Sheets

(56) References Cited

U.S. PATENT DOCUMENTS

| | | |
|---|---|---|
| 3,929,678 A | 12/1975 | Laughlin |
| 3,967,921 A | 7/1976 | Haberli et al. |
| 4,020,156 A | 4/1977 | Murray et al. |
| 4,051,081 A | 9/1977 | Jabs et al. |
| 4,089,945 A | 5/1978 | Brinkman et al. |
| 4,149,551 A | 4/1979 | Benjamin et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De Marco et al. |
| 4,536,361 A | 8/1985 | Torobin |
| 4,565,647 A | 1/1986 | Llenado |
| D286,450 S | 10/1986 | Tovey |
| 4,663,158 A | 5/1987 | Wolfram et al. |
| 4,710,374 A | 12/1987 | Grollier et al. |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,104,646 A | 4/1992 | Bolich, Jr. |
| 5,106,609 A | 4/1992 | Bolich, Jr. |
| 5,166,276 A | 11/1992 | Hayama et al. |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,476,597 A | 12/1995 | Sakata et al. |
| 5,501,238 A | 3/1996 | Borstel et al. |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| 5,885,561 A | 3/1999 | Flemming et al. |
| D407,640 S | 4/1999 | Crapser et al. |
| D408,223 S | 4/1999 | Henry |
| 5,911,224 A | 6/1999 | Berger |
| 5,925,603 A | 7/1999 | D Angelo |
| 5,955,419 A | 9/1999 | Barket, Jr. et al. |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D442,739 S | 5/2001 | Friesenhahn |
| D443,389 S | 6/2001 | Friesenhahn |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D484,749 S | 1/2004 | Garraway |
| 6,790,814 B1 | 9/2004 | Marin |
| 6,800,295 B2 | 10/2004 | Fox |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| D739,227 S | 9/2015 | Mitchell et al. |
| D740,928 S | 10/2015 | Bruining et al. |
| 9,198,838 B2 | 12/2015 | Glenn, Jr. |
| D769,522 S | 10/2016 | Venet |
| 9,539,444 B2 | 1/2017 | Kinoshita et al. |
| D793,025 S | 8/2017 | Slusarczyk et al. |
| D797,551 S | 9/2017 | Chatterton |
| D798,143 S | 9/2017 | Chatterton |
| 9,849,075 B2 | 12/2017 | Tokunaga et al. |
| D808,583 S | 1/2018 | Zietek |
| 10,294,586 B2 | 5/2019 | Sivik et al. |
| D851,344 S | 6/2019 | Carlson et al. |
| D857,156 S | 8/2019 | Hani |
| 10,413,496 B2 | 9/2019 | Pistorio et al. |
| D862,020 S | 10/2019 | Gorrell et al. |
| D866,893 S | 11/2019 | Hunt et al. |
| D867,717 S | 11/2019 | Chavez |
| D868,953 S | 12/2019 | Mckendree |

(56) References Cited

U.S. PATENT DOCUMENTS

| | | |
|---|---|---|
| 10,569,286 B2 | 2/2020 | Anderson et al. |
| 10,694,917 B2 | 6/2020 | Dreher et al. |
| 10,765,613 B2 | 9/2020 | Marsh |
| D910,434 S | 2/2021 | Tan et al. |
| D910,457 S | 2/2021 | Lee |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan |
| 2003/0082129 A1 | 5/2003 | Buckingham et al. |
| 2003/0099691 A1 | 5/2003 | Lydzinski et al. |
| 2003/0099692 A1 | 5/2003 | Lydzinski et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2005/0069575 A1 | 3/2005 | Fox |
| 2005/0095215 A1* | 5/2005 | Popp ............... A61Q 5/006 424/70.21 |
| 2005/0136780 A1 | 6/2005 | Clark et al. |
| 2005/0137272 A1 | 6/2005 | Gaserod |
| 2005/0159730 A1 | 7/2005 | Kathrani et al. |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0024256 A1 | 2/2006 | Wells et al. |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0128592 A1 | 6/2006 | Ross |
| 2006/0159730 A1 | 7/2006 | Simon |
| 2006/0228319 A1 | 10/2006 | Vona, Jr. et al. |
| 2006/0274263 A1 | 12/2006 | Yacktman et al. |
| 2007/0028939 A1 | 2/2007 | Mareri et al. |
| 2007/0099813 A1 | 5/2007 | Luizzi |
| 2007/0110700 A1* | 5/2007 | Wells ............... A61K 8/4933 424/70.21 |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2007/0237736 A1 | 10/2007 | Burgo et al. |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0139672 A1* | 6/2008 | Rozsa ............... A61Q 17/005 514/772 |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn, Jr. et al. |
| 2009/0263342 A1 | 10/2009 | Glenn, Jr. |
| 2010/0018641 A1 | 1/2010 | Branham |
| 2010/0150858 A1 | 6/2010 | Runglertkriangkrai |
| 2010/0150976 A1 | 6/2010 | Schnitzler |
| 2010/0167971 A1 | 7/2010 | Glenn, Jr. et al. |
| 2010/0173817 A1 | 7/2010 | Glenn, Jr. et al. |
| 2010/0286011 A1 | 11/2010 | Glenn, Jr. et al. |
| 2010/0291165 A1 | 11/2010 | Glenn, Jr. et al. |
| 2011/0023240 A1 | 2/2011 | Fossum |
| 2011/0027328 A1 | 2/2011 | Baig et al. |
| 2011/0028374 A1 | 2/2011 | Fossum et al. |
| 2011/0033509 A1 | 2/2011 | Simon |
| 2011/0165110 A1 | 7/2011 | Kinoshita et al. |
| 2011/0182956 A1 | 7/2011 | Glenn, Jr. et al. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-oh et al. |
| 2011/0287687 A1 | 11/2011 | Kramer et al. |
| 2012/0021026 A1 | 1/2012 | Glenn, Jr. |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |
| 2012/0237576 A1 | 9/2012 | Gordon |
| 2012/0270029 A1 | 10/2012 | Glenn, Jr. et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0303419 A1 | 11/2013 | Glenn, Jr. et al. |
| 2014/0105942 A1 | 4/2014 | Pistorio et al. |
| 2014/0329428 A1 | 11/2014 | Glenn, Jr. |
| 2014/0356307 A1 | 12/2014 | Yang et al. |
| 2015/0017218 A1 | 1/2015 | Pettigrew et al. |
| 2015/0250701 A1 | 9/2015 | Hamersky et al. |
| 2015/0290109 A1 | 10/2015 | Simonnet et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0101026 A1 | 4/2016 | Pratt |
| 2016/0101204 A1 | 4/2016 | Lynch |
| 2016/0143827 A1 | 5/2016 | Castan Barberan et al. |
| 2016/0158134 A1 | 6/2016 | Disalvo |
| 2016/0243007 A1 | 8/2016 | Constantine et al. |
| 2016/0250109 A1 | 9/2016 | Dreher et al. |
| 2016/0361242 A1 | 12/2016 | Durtschi et al. |
| 2016/0367104 A1 | 12/2016 | Dreher et al. |
| 2017/0056300 A1 | 3/2017 | Constantine et al. |
| 2017/0056301 A1 | 3/2017 | Constantine et al. |
| 2017/0121641 A1 | 5/2017 | Smith |
| 2017/0335080 A1 | 11/2017 | Mao et al. |
| 2018/0028435 A1 | 2/2018 | Punsch et al. |
| 2018/0311135 A1 | 11/2018 | Chang et al. |
| 2018/0311137 A1 | 11/2018 | Mckiernan et al. |
| 2018/0333339 A1 | 11/2018 | Hamersky |
| 2018/0334644 A1 | 11/2018 | Hamersky et al. |
| 2018/0360702 A1 | 12/2018 | Demarcq et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0093710 A1 | 3/2020 | Hamersky |
| 2020/0214946 A1 | 7/2020 | Chan et al. |

(56) References Cited

U.S. PATENT DOCUMENTS

| | | |
|---|---|---|
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0147763 A1 | 5/2021 | Tan et al. |
| 2021/0161780 A1 | 6/2021 | Zhao et al. |

FOREIGN PATENT DOCUMENTS

| | | |
|---|---|---|
| CN | 1268558 | 10/2000 |
| CN | 1357613 A | 7/2002 |
| CN | 1530431 A | 9/2004 |
| CN | 1583991 A | 2/2005 |
| CN | 106726634 A | 5/2017 |
| CN | 109589279 B | 3/2020 |
| DE | 19607851 A1 | 9/1997 |
| DE | 10331767 A1 | 2/2005 |
| DE | 102010002863 A1 | 9/2011 |
| DE | 102010026747 A1 | 1/2012 |
| DE | DM100932 | 4/2018 |
| DE | DM100938 | 4/2018 |
| DE | DM101063 | 5/2018 |
| DE | DM101100 | 5/2018 |
| DE | DM101101 | 5/2018 |
| EP | 609808 A1 | 8/1994 |
| EP | 855178 A2 * | 7/1998 ............ A61K 8/365 |
| EP | 0858828 A1 | 8/1998 |
| EP | 1206933 A1 | 5/2002 |
| EP | 1217987 B1 | 12/2004 |
| EP | 1160311 B1 | 3/2006 |
| EP | 1808157 A1 | 7/2007 |
| EP | 1958532 A2 | 8/2008 |
| EP | 2085434 A1 | 8/2009 |
| EP | 1317916 B1 | 10/2010 |
| EP | 2777688 A1 * | 9/2014 ............... A61K 8/25 |
| FR | 2871685 A1 | 12/2005 |
| FR | 2886845 A1 | 12/2006 |
| FR | 2992217 A1 | 12/2013 |
| GB | 2235204 A | 2/1991 |
| GB | 2355008 A | 4/2001 |
| JP | 58021608 | 2/1983 |
| JP | S58216109 A | 12/1983 |
| JP | S6272609 A | 4/1987 |
| JP | S6272610 A | 4/1987 |
| JP | S6281432 A | 4/1987 |
| JP | H01172319 A | 7/1989 |
| JP | H01313418 A | 12/1989 |
| JP | H0275650 A | 3/1990 |
| JP | H05344873 A | 12/1993 |
| JP | H0617083 A | 1/1994 |
| JP | 0753349 | 2/1995 |
| JP | H0789852 A | 4/1995 |
| JP | H08325133 A | 12/1996 |
| JP | H09216909 A | 8/1997 |
| JP | H10251371 A | 9/1998 |
| JP | H11322591 A | 11/1999 |
| JP | 2000053998 A | 2/2000 |
| JP | 2003073700 A | 3/2003 |
| JP | 2003082397 A | 3/2003 |
| JP | 2003113032 A | 4/2003 |
| JP | 2004256799 A | 9/2004 |
| JP | 2004345983 A | 12/2004 |
| JP | 2005171063 A | 6/2005 |
| JP | 2007091954 A | 4/2007 |
| JP | 2007197540 A | 8/2007 |
| KR | 20020003442 A | 1/2002 |
| WO | 8301943 A1 | 6/1983 |
| WO | 9514495 A1 | 6/1995 |
| WO | 0112134 A2 | 2/2001 |
| WO | 0119948 A1 | 3/2001 |
| WO | 0125393 A1 | 4/2001 |
| WO | 200125322 A1 | 4/2001 |
| WO | 2001054667 A1 | 8/2001 |
| WO | 2004032859 A1 | 4/2004 |
| WO | WO-2004035016 A1 * | 4/2004 ............ A61K 8/342 |
| WO | 2005003423 A1 | 1/2005 |
| WO | 2005070374 A1 | 8/2005 |
| WO | 2005075547 A1 | 8/2005 |
| WO | 2007033598 A1 | 3/2007 |
| WO | 2007093558 A1 | 8/2007 |
| WO | 2009019571 A1 | 2/2009 |
| WO | 2009095891 A1 | 8/2009 |
| WO | 2010077627 A2 | 7/2010 |
| WO | 2010085569 A1 | 7/2010 |
| WO | 2011113501 A1 | 9/2011 |
| WO | 2012120199 A1 | 9/2012 |
| WO | 2012172207 A2 | 12/2012 |
| WO | 2013150044 A2 | 10/2013 |
| WO | 2018023180 A1 | 2/2018 |
| WO | 2018098542 A1 | 6/2018 |
| WO | 2019001940 A1 | 1/2019 |
| WO | 2019014868 A1 | 1/2019 |
| WO | 2019090098 A1 | 5/2019 |

OTHER PUBLICATIONS

Anonymous "P8136 Poly(vinyl alcohol)" Internet article, [Online] XP002538935 retrieved from the Internet: URL:hllp/20NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009.

Briscoe et al. "The effects of hydrogen bonding upon the viscosity of aqueous poly( vinyl alcohol) solutions," from Polymer, 41 (2000), pp. 3851-3860.

Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.

Hildebrand, T., et al. "Quantification of bone microarchitecture with the structure mode index", Computer Methods in Biomechanics and Biomedical Engineering, vol. 1, Jan. 14, 1997, pp. 15-23.

How Gemz work?, Gemz Hair Care, published on Oct. 1, 2018, retrieved on Apr. 27, 2021, retrieved from the Internet URL: https://www.youtube.com/watch?v=ts1waYk43g4.

https://www.craftcuts.com/hexagon-craft-shape.htmlHexagon wood cutouts, www.craftcuts.com, 1 page, reviewed as early as May 2018 (Year: 2018).

Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014].

Michelle Villett, Why You Need a Sulfate-Free Shampoo, The Skincare Edit, updated date: Jan. 25, 2019, Original publication date: Feb. 22, 2016 (Year: 2016), 7 pages.

Miller Robert et al. "Bio-basedpropanediol boosts preservative efficacy",Personal Care,Apr. 1, 2012 (Apr. 1, 2012), pp. 1-4,XP055773579.

N Konate et al: "Sustainably SourcedPentylene Glycol—a Green All-Rounder",SOFW Journal: Seifen, Ole, Fette, Wachse,vol. 10, No. 142,Oct. 1, 2016 (Oct. 1, 2016), pp. 44-51,XP055747004.

Okasaka et al., "Evaluation of Anionic Surfactants Effects on the Skin Barrier Function Based on Skin Permeability", Pharmaceutical Development and Technology, vol. 24, No. 1, Jan. 23, 2018, pp. 99-104.

Product Review: Gemz Solid Shampoo, Travel as Much, published on Mar. 19, 2019, retrieved on Apr. 27, 2021, retrieved from the Internet URL: https://travelasmuch.com/gemz-solid-shampoo-review/.

Unpublished U.S. Appl. No. 17/209,292, filed Mar. 23, 2021, to Jennifer Mary Marsh et. al.

Vaughan, C.D. "Solubility, Effects in Product, Package, Penetration and Preservation", Cosmetics and Toiletries, vol. 103, Oct. 1988.

Veslerby, A.: "Star Volume in Bone Research: A Histomorphometric Analysis of Trabecular Bone Structure UsingVertical Sections", Anal Rec: Feb. 1993, 232(2), pp. 325-334.

Zhang et al. "Study on Morphology of Electrospun Poly( vinyl alcohol) Mats," European Polymer Journal 41 (2005), pp. 423-432.

All Office Actions; U.S. Appl. No. 17/398,024, filed Aug. 10, 2021.

(56) References Cited

OTHER PUBLICATIONS

All Office Actions; U.S. Appl. No. 17/398,025, filed Aug. 10, 2021.
All Office Actions; U.S. Appl. No. 17/398,020, filed Aug. 10, 2021.
Unpublished U.S. Appl. No. 17/398,020, filed Aug. 10, 2021, to Jean Jianqun Zhao et. al.
Unpublished U.S. Appl. No. 17/398,024, filed Aug. 10, 2021, to Jean Jianqun Zhao et. al.
Unpublished U.S. Appl. No. 17/398,025, filed Aug. 10, 2021, to Jean Jianqun Zhao et. al.

* cited by examiner

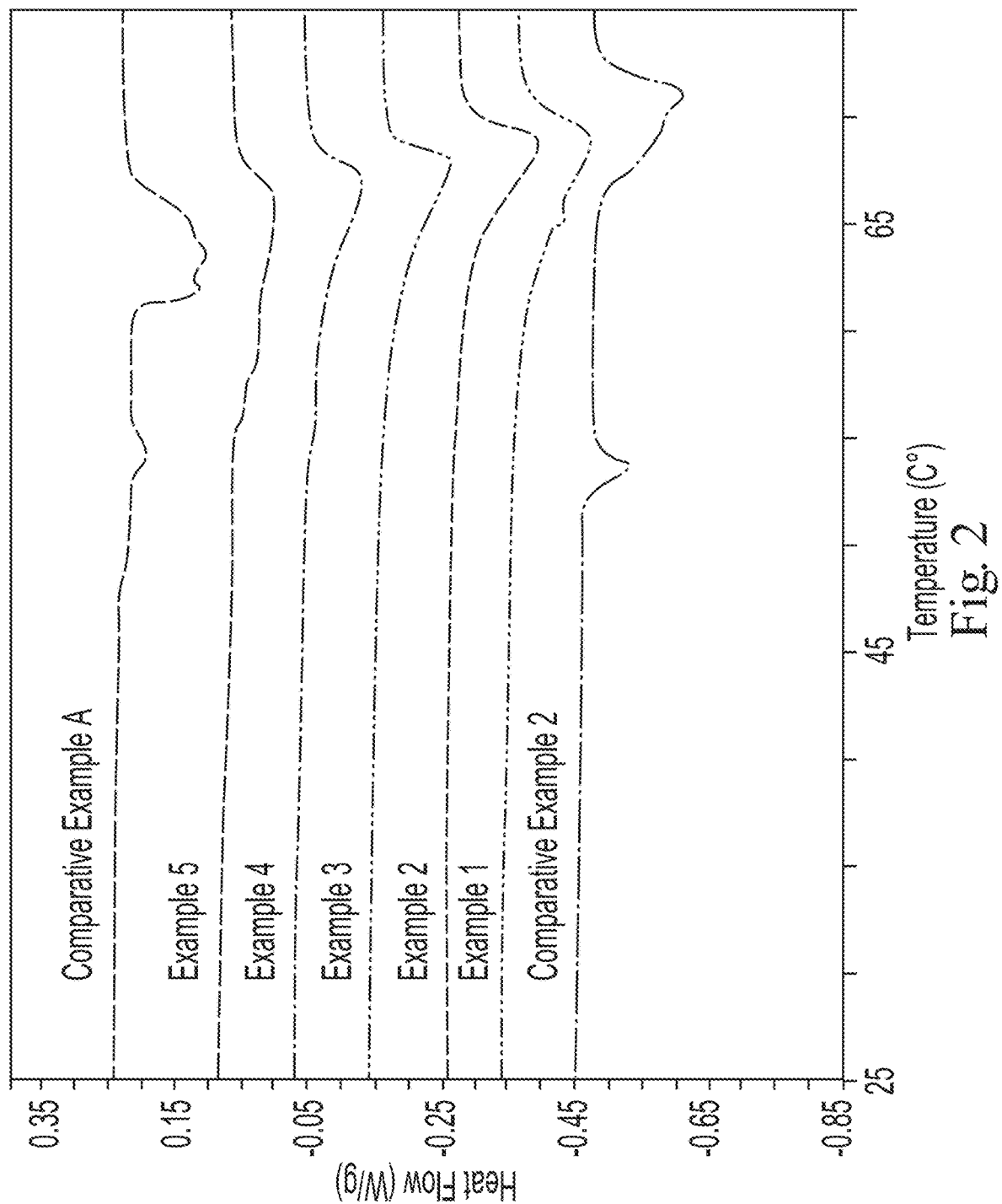

HAIR CONDITIONER COMPOSITIONS CONTAINING BEHENAMIDOPROPYL DIMETHYLAMINE

FIELD OF THE INVENTION

The present invention relates to hair conditioner compositions, more particularly to hair conditioner compositions comprising behenamidopropyl dimethylamine cationic surfactant.

BACKGROUND OF THE INVENTION

A variety of approaches have been developed to condition the hair. These approaches range from post-shampoo application of hair conditioners such as leave-on and rinse-off products, to hair conditioning shampoos which attempt to both clean and condition the hair from a single product.

Although some consumers prefer the ease and convenience of a shampoo which includes conditioners, a substantial proportion of consumers prefer the more conventional conditioner formulations which are applied to the hair as a separate step from shampooing, usually after shampooing. Conditioning formulations can be in the form of rinse-off products or leave-on products, and can be in the form of an emulsion, cream, gel, spray, and mousse. Such consumers who prefer the conventional conditioner formulations value the relatively higher conditioning effect, or convenience of changing the amount of conditioning depending on the condition of hair or amount of hair.

Some consumers want a reduction or elimination of certain ingredients, including certain surfactants and preservatives, in hair care products. Some consumers want the ingredients in their hair care products to be EWG VERIFIED™, free of any of the ingredients that Whole Foods® lists as unacceptable for body care and be categorized as "risk-free" (green dot) by the Yuka® Application.

However, modifying the conditioner can negatively impact the product. For example, modifying the cationic surfactant can decrease conditioning performance and modifying the preservation system can have a negative impact on microbiological safety requirements.

Therefore, there is a need for a conditioner composition with an effective surfactant and preservation system that that is EWG VERIFIED™, does not contain any of the ingredients that Whole Foods® Market lists as unacceptable, and is categorized as "risk-free" by Yuka® Application.

SUMMARY OF THE INVENTION

A hair conditioner composition can contain: (a) an aqueous carrier; (b) from about 2.5 wt % to about 6.7 wt % of a behenamidopropyl dimethylamine; (c) from about 3 wt % to about 8 wt % of a fatty alcohol; (d) less than 1.5 wt % of a salt selected from the group consisting of sodium benzoate, sodium salicylate, sodium chloride, sodium carbonate, sodium borate, sodium acetate, sodium citrate, potassium benzoate, potassium acetate, calcium gluconate, calcium chloride, potassium sorbate, and combinations thereof; wherein the molar ratio of behenamidopropyl dimethylamine to fatty alcohol is from about 7:50 to about 4:5; wherein the composition comprises a uniform gel network; wherein the composition comprises d-spacing of less than 32 nm, as measured according to the d-spacing (Lβ-basal spacing) of Lamella Gel Network Test Method.

A hair conditioner composition comprising: (a) an aqueous carrier; (b) from about 2.5 wt % to about 6.25 wt % behenamidopropyl dimethylamine; (c) a fatty alcohol selected from the group consisting of stearyl alcohol, brassical alcohol, cetyl alcohol, and combinations thereof; (d) a preservation system comprising (i) from about 0.1% to about 0.5% sodium benzoate, by weight of the composition; (ii) from about 0.3% to about 1.5% of a second composition selected from the group consisting of glycol, glyceryl ester, and combinations thereof; wherein the molar ratio of sodium benzoate to the second composition is from about 1:4 to about 1:1; wherein the molar ratio of behenamidopropyl dimethylamine to fatty alcohol is from about 3:20 to about 3:4; wherein the composition comprises a uniform gel network; wherein the composition comprises d-spacing of from about 15 nm to about 30 nm, as measured according to the d-spacing (Lβ-basal spacing) of Lamella Gel Network Test Method.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 2 shows the melt transition behavior of the gel network, as measured by the Differential Scanning calorimetry (DSC) Test Method, of Examples 1-5 and Comparative Examples A and B;

DETAILED DESCRIPTION OF THE INVENTION

While the specification concludes with claims particularly pointing out and distinctly claiming the invention, it is believed that the present invention will be better understood from the following description.

Hair conditioners are used to improve the feel, appearance, and manageability of the hair. Hair conditioning compositions generally include cationic surfactant(s), high melting point fatty compound(s) having a melting point of greater than 25° C. and in some examples from 40 to 85° C., and an aqueous carrier. The ingredients in current hair conditioners, including the cationic surfactant and preservation system, are generally recognized as safe and effective. However, there is growing demand from some consumers for a conditioner product and/or a preservation system that meets at least one, two, or all three of the following standards:

EWG VERIFIED™ (according to the criteria, as of Nov. 25, 2019), which includes meeting the Environmental Working Group's (EWG) criteria including avoiding EWG's ingredients of concern, having fully transparent labeling, and using good manufacturing practices, in addition to other criteria described in EWG's Licensing Criteria: Personal Care Products (2019).

Does not contain any of ingredients that Whole Foods® lists as unacceptable lists as unacceptable in its *Premium Body Care Unacceptable Ingredients* (July 2018)

Categorized as "risk-free" (green dot) by the Yuka® Application (March 2019)

However, replacing traditional cationic surfactants, such as behentrimonium chloride (BTMAC), which is restricted by the Environmental Working Group (EWG) for use in the cosmetic products as of Nov. 25, 2019 and/or stearamidopropyl dimethylamine (SAPDMA), which is an unacceptable ingredient listed on the Whole Foods® *Premium Body Care Unacceptable Ingredients* (July 2018), and preservatives with ingredients that meet the standards, listed above, while maintaining product performance and antimicrobial effectiveness can be challenging.

Figure 1A:
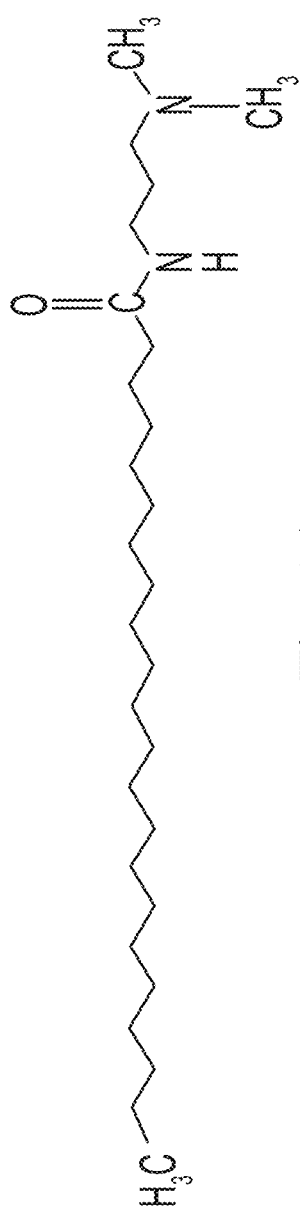
FIG. 1A shows the chemical structure for behenamidopropyl dimethylamine (BAPDMA)
Figure 1B:
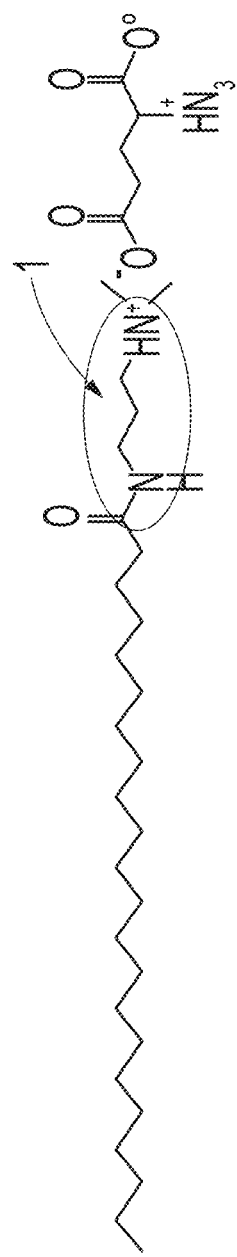
FIG. 1B shows the chemical structure of BAPDMA after it has been activated with l-glutamic acid.

Behenamidopropyl dimethylamine (BAPDMA) was identified as a cationic surfactant that can meet the standards, above. However, it can be hard to formulate effective conditioner compositions that contain BAPDMA because BAPDMA is a $C_{22}$ amidoamine with the structure shown in FIG. 1A. BAPDMA needs to be activated with an acid, like l-glutamic acid, to become cationic. However, after the cationic surfactant is formed, as shown in the structure in FIG. 1B, it has a large head group 1. This large head group tends to affect the surfactant and fatty alcohol(s) packing during the melt stage when the gel network is formed. This makes the d-spacing in the gel network in the conditioner composition larger, which generally leads to a conditioner with poor wet conditioning performance.

It was surprisingly found that the d-spacing in the inventive conditioner compositions (see Table 3 to Table 7, below) is less than 30 nm. It is believed that conditioners with d-spacing of less than 30 nm can provide good conditioning, clean feel, volume, and consumer preferred shear stress.

While not willing to be bound by theory, it is believed that the molar ratio of BAPDMA to fatty alcohol(s) and the addition of salts including sodium benzoate, can result in a conditioner composition with d-spacing that is less than 30 nm that provides good conditioning performance including a good slippery feel and wet detangling.

Table 1, below, compares the d-spacing of four commercially available conditioner compositions to Ex. 1 to Ex. 28 in Table 3 to Table 7. It was found that the d-spacing of Ex. 1 to 28 was similar to Herbal Essences® Honey & Vitamin B Conditioner, which contains BTMAC and the d-spacing was lower than the other examples, including John Frieda® Sheer Blond Brightening Conditioner, which contains the same cationic polymer (BAPDMA) as Ex. 1-28.

TABLE 1 d-Spacing of Current Products vs. Examples 1-28

| | Herbal Essences® Honey & Vitamin B Conditioner[1] | Herbal Essences® Cucumber & Green Tea Conditioner[2] | Herbal Essences® Refresh Blue Ginger[3] | John Frieda® Sheer Blond Brightening Conditioner[4] | Ex. 1 to Ex. 28 (Table 3 to Table 7) |
|---|---|---|---|---|---|
| Primary Cationic Surfactant | BTMAC | SAPDMA | SAPDMA | BAPDMA | BAPDMA |
| Gel network d-spacing (nm) | 24.2 | 32.6 | 34 | 35.1 | 20.8 to 26.8 |

[1]Lot # 83565395LF, purchased at Target ®, Mason, Ohio 2019
[2]Lot # 82325395LK, purchased at Target ®, Mason, Ohio 2019
[3]Lot # 82165395LC, purchased at Target ®, Mason, Ohio 2019
[4]Lot # X0J11438 B, purchased at Target ®, Mason, Ohio 2019

Furthermore, the conditioners in Ex. 1 to Ex. 28 (Table 3 to Table 7), had a uniform gel network, as indicated by the single peak when the Differential Scanning calorimetry Test Method was performed.

Also, conditioner compositions that provide good wet conditioning may weigh down hair causing a loss of dry hair volume and/or may cause the hair to feel dirty and/or oily quickly, which can result in consumers washing their hair more frequently. It was found that the hair conditioner compositions of Ex. 1 to Ex. 35 may not only provide good hair conditioning but may also give good hair volume and/or provide a long-lasting clean feel, allowing less washing frequency.

Furthermore, Table 9 and Table 10, below, include examples that have a sodium benzoate preservative, which meets the standards. However, if the conditioner composition had a smooth and creamy consistency, then the level of sodium benzoate was too low to effectively inhibit the growth of microbes. When the level of sodium benzoate was increased, the conditioner composition was too thin to easily apply with a user's hands, which can significantly impact product performance and the usage experience. As shown in Table 11 and described in accompanying text, a preservation system with sodium benzoate and a glycol, such as caprylyl glycol, or glyceryl esters, such as glyceryl caprylate/caprate and glyceryl caprylate (and) glyceryl undecylenate can be effective if the proper levels of each ingredient are added.

It was found that a preservation system that contains sodium benzoate and a second composition selected from the group consisting of glycols, glyceryl esters, and combinations thereof contains all of the ingredients that have a EWG rating score of equal to or less than 3, can be EWG VERIFIED™, may not contain any of the ingredients that Whole Foods® Market lists as unacceptable, and can categorized as "risk-free" by the Yuka® Application, can maintain antimicrobial effectiveness, and can provide good conditioning performance.

The second composition can contain a glycol and/or a glyceryl ester. Glycols and glyceryl esters both have two —OH groups on the molecule. Non-limiting examples of glycols can include butylene glycol, pentylene glycol, hexylene glycol, 1,2-hexanediol, caprylyl glycol, decylene glycol (1,2-decanediol) and mixtures thereof. In one example, the glycol can be carpylyl Non-limiting examples of glycerol esters can include glyceryl caprylate, glyceryl caprate, glyceryl undecylenate and mixtures thereof.

In some examples, the cationic surfactant, the preservation system and/or the conditioner can also meet the COSMOS-standard (Jan. 1, 2019). The conditioner compositions containing this preservation system can have a uniform, smooth, creamy appearance and have an effective preservation system where the level of microbes (both bacteria and fungi) is undetectable (>99.99% reduction) as determined by the Bacterial and Fungal Microbial Susceptibility Test Methods, as described herein.

The conditioner composition and/or preservation system can be free of or substantially free of certain preservatives, in particular preservatives that do not meet one or more of the requirements, isothiazolinones including 5-chloro-2-methyl-4-isothiazolin-3-one and 2-methyl-4-isothiazolin-3-one (commercially available as Kathon™ CG from Dow®), benzyl alcohol, phenoxyethanol, cyclohexylglycerin, and/or parabens. The conditioner composition can be free of or substantially free of ethylenediaminetetraacetic acid (EDTA) and salts thereof.

In addition to meeting the standards for a cationic surfactant and preservation system, some consumers prefer a conditioner composition that is free of or substantially free of the following: silicone, propellants, phthalates, parabens, isothiazolinones (e.g. Kathon™), phenoxyethanols, dyes, sulfates, and/or formaldehyde donors. The conditioner composition can also be vegan.

The conditioner composition can be free of or substantially free of behentrimonium chloride, cetrimonium chloride, and/or stearamidopropyl dimethylamine.

The conditioner composition can contain less than 6.75 wt % BAPDMA, alternatively less than about 6.50 wt % BAPDMA, alternatively less than about 6.25 wt % BAPDMA. The conditioner composition can contain from about 2 wt % to about 6.7 wt % BAPDMA, alternatively from about 2.2 wt % to about 6.5 wt %, alternatively from about 2.5 wt % to about 6.25 wt % BAPDMA, alternatively from about 2.75 wt % to about 6 wt %.

The conditioner composition can contain a fatty alcohol selected from the group consisting of stearyl alcohol, brassical alcohol, and cetyl alcohol. The conditioner composition can contain less than 8 wt % fatty alcohol, alternatively less than 7.5 wt %, alternatively less than 7 wt %. The conditioner composition can contain from about 2.5 wt % to about 9 wt % fatty alcohol, alternatively from about 3 wt % to about 8 wt %, alternatively from about 3.25 wt % to about 7.5 wt %, alternatively from about 3.5 wt % to about 7 wt %, alternatively from about 4 wt % to about 6.7 wt %.

The conditioner composition can have a total gel network (GN) content (BAPDMA+fatty alcohol(s) (FAOH)) of from about 0.1 to about 0.6 molar, alternatively from about 0.2 to about 0.5 molar, alternatively from about 0.3 to about 0.4 molar.

The conditioner composition can have a molar ratio of stearyl alcohol (C18 fatty alcohol) to total FAOH of from about 1:10 to about 1:1, alternatively from about 1:5 to about 9:10, alternatively from about 3:10 to about 4:5, and alternatively from about 2:5 to about 7:10.

The conditioner composition can have a molar ratio of acid to BAPDMA ratio of from about 1:2 to about 7:4, alternatively from about 3:5 to about 1:2, alternatively from about 7:10 to about 5:4, and alternatively from about 4:5 to about 1.3:1.

The conditioner composition can have a molar ratio of BAPDMA to FAOH from about 3:25 to about 9:10, from about 7:50 to about 4:5, from about 3:20 to about 3:4, from about 17:100 to about 7:10, and alternatively from about 9:50 to about 2:3.

The conditioner composition can have d-spacing of less than 32 nm, alternatively less than 30 nm, and alternatively less than 28 nm. The conditioner composition can have d-spacing from about 10 nm to about 30 nm, alternatively from about 15 nm to about 30 nm, alternatively from about 17 nm to about 29 nm, alternatively from about 18 nm to about 28 nm, and alternatively from about 20 nm to about 27 nm. The d-spacing determined by the d-spacing (Lβ-basal spacing) of Lamella Gel Network Test Method, described herein.

The conditioner composition can contain from about 0.2 wt % to about 1.5 wt % preservation system, alternatively from about 0.3 wt % to about 1.25 wt % preservation system, alternatively from about 0.4 wt % to about 1 wt % preservation system, alternatively from 0.5 wt % to about 0.8 wt % preservation system, and alternatively from about 0.6 wt % to about 0.8 wt % preservation system.

The conditioner composition can contain from about 0.05 wt % to about 0.8 wt % sodium benzoate, alternatively 0.1 wt % to about 0.5 wt % sodium benzoate, alternatively from about 0.2 wt % to about 0.4 wt % sodium benzoate. The conditioner composition can contain sodium benzoate and can contain less than 2% sodium benzoate, alternatively less than 1.5% sodium benzoate, alternatively less than 1% sodium benzoate, alternatively less than 0.8% sodium benzoate, alternatively less than 0.6 wt % sodium benzoate, and alternatively less than 0.5% sodium benzoate.

The preservation system can contain from about 20% to about 50% sodium benzoate, by weight of the preservation system, alternatively from about 25% to about 50% sodium benzoate, by weight of the preservation system, from about 30% to about 50% sodium benzoate, by weight of the preservation system, and from about 30% to about 40% sodium benzoate, by weight of the preservation system.

The conditioner composition can contain from about 0.3 wt % to about 1.5 wt % of a second composition, alternatively from about 0.32 wt % to about 1 wt %, alternatively from about 0.33 wt % to about 0.8 wt %, alternatively from about 0.34 wt % to about 0.6 wt %, alternatively from about 0.35 wt % to about 0.5 wt %, alternatively from about 0.37 wt % to about 0.45 wt %, and alternatively from about 0.38 wt % to about 0.43 wt %. If the conditioner composition contains too much glycol and/or glyceryl esters the gel network structure may be destroyed, and the conditioner will not have consumer acceptable rheology and/or performance.

The preservation system can contain from about 50% to about 80% of the second composition, by weight of the preservation system, alternatively from about 50% to about 75%, by weight of the preservation system, alternatively from about 50% to about 70%, by weight of the preservation system, and alternatively from about 50% to about 67%, by weight of the preservation system.

The weight ratio of sodium benzoate to the second composition can be from about 1:4 to about 1:1, alternatively from about 1:3 to about 1:1, alternatively from about 1:2 to about 1:1, and from about 1:1.7 to about 1:1.

The conditioner composition can have a shear stress from about 50 Pa to about 600 Pa, alternatively from about 75 Pa to about 575 Pa, alternatively from about 100 Pa to about 565 Pa, alternatively from about 105 Pa to about 550 Pa, alternatively from about 120 Pa, to about 500 Pa, and alternatively from about 125 Pa to about 450 Pa. The shear stress can be determined using the Shear Stress Test Method, described hereafter.

The conditioner composition can have a pH of less than 5. Alternatively, the conditioner composition can have a pH from about 2.5 to about 5, alternatively from about 3.5 to about 4.5. The pH can be determined using the pH Test Method, described hereafter.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of."

As used herein, the terms "include," "includes," and "including," are meant to be non-limiting and are understood to mean "comprise," "comprises," and "comprising," respectively.

As used herein, the term "free of" means that 0% of an ingredient was intentionally added to the conditioner composition, or the conditioner composition comprises 0% of an ingredient by total weight of the composition, thus no detectable amount of the stated ingredient.

The term "substantially free of" as used herein means less than 0.5%, less than 0.3%, less than 0.1%, less than 0.05%, less than 0.01%, or less than an immaterial amount of a stated ingredient by total weight of the composition.

As used herein, "mixtures" is meant to include a simple combination of materials and any compounds that may result from their combination.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cationic Surfactant

The compositions of the present invention can comprise a cationic surfactant. The cationic surfactant can be included in the composition at a level of from about 0.1%, alternatively from about 0.5%, alternatively from about 0.8%, alternatively from about 1.0%, and to about 20%, alternatively to about 10%, alternatively to about 8.0%, alternatively to about 6.0% by weight of the composition, in view of providing the benefits of the present invention.

The surfactant can be water-insoluble. In the present invention, "water-insoluble surfactants" means that the surfactants have a solubility in water at 25° C. of alternatively below 0.5 g/100 g (excluding 0.5 g/100 g) water, alternatively 0.3 g/100 g water or less.

Cationic surfactant can be one cationic surfactant or a mixture of two or more cationic surfactants. Alternatively, the cationic surfactant is selected from: a mono-long alkyl amine; a di-long alkyl quaternized ammonium salt; a mono-long alkyl cationic neutralized amino acid esters; a combination of a mono-long alkyl amine and a di-long alkyl quaternized ammonium salt; and a combination of a mono-long alkyl amine and a mono-long alkyl cationic neutralized amino acid esters.

In some examples, the conditioner composition can be substantially free of or free of cationic surfactants that have a quaternized ammonium salt.

Mono-Long Alkyl Amine

Mono-long alkyl amine can include those having one long alkyl chain of alternatively from 19 to 30 carbon atoms, alternatively from 19 to 24 carbon atoms, alternatively from 20 to 24 carbon atoms, alternatively from 20 to 22 alkyl group. Mono-long alkyl amines can include mono-long alkyl amidoamines Primary, secondary, and tertiary fatty amines can be used.

Tertiary amido amines having an alkyl group of from about 19 to about 22 carbons. Exemplary tertiary amido amines include: behenamidopropyldimethylamine, behenamidopropyldiethylamine, behenamidoethyldiethylamine, behenamidoethyldimethylamine, brassicamidopropyldimethylamine, brassicamidopropyldiethylamine, brassicamidoethyldiethylamine, brassicamidoethyldimethylamine Amines in the present invention are disclosed in U.S. Pat. No. 4,275,055, Nachtigal, et al.

In some examples, the conditioner composition can be substantially free of or free of stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, arachidamidopropyldimethylamine, arachidamidopropyldiethylamine, arachidamidoethyldiethylamine, arachidamidoethyldimethylamine, and/or diethylaminoethylstearamide.

These amines are used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; alternatively lactic acid, citric acid, at a molar ratio of the amine to the acid of from about 1:0.3 to about 1:2, alternatively from about 1:0.4 to about 1:1. The conditioner composition can contain from about 0.25 wt % to about 6 wt % acid, alternatively from about 0.4 wt % to about 5 wt % acid, from about 0.5 wt % to about 4 wt % acid, and alternatively from about 0.6 wt % to about 3 wt % acid.

In some examples, the conditioner composition can be free of mono long alkyl quaternized ammonium salts.

Di-Long Alkyl Quaternized Ammonium Salts

When used, di-long alkyl quaternized ammonium salts are alternatively combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts can have two long alkyl chains of from 12 to 30 carbon atoms, alternatively from 16 to 24 carbon atoms, alternatively from 18 to 22 carbon atoms. Such di-long alkyl quaternized ammonium salts can have the formula (I):

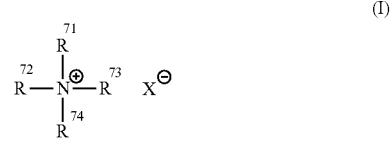

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Alternatively, two of $R^{71}$, $R^{72}$, $R^{73}$ and $R^{74}$ are selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Di-long alkyl cationic surfactants can include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound can be included in the composition at a level of from about 1.0%, alternatively from about 1.5%, alternatively from about 2.0%, alternatively from about 2.5%, even alternatively from about 3%, and to about 30%, alternatively to about 15%, alternatively to about 8.0%, alternatively to about 7% by weight of the composition, in view of providing the benefits of the present invention.

The high melting point fatty compound can have a melting point of 25° C. or higher, alternatively 40° C. or higher, alternatively 45° C. or higher, alternatively 47° C. or higher, alternatively 49° C. or higher, in view of stability of the emulsion especially the gel network. Alternatively, such melting point is up to about 90° C., alternatively up to about 80° C., alternatively up to about 75° C., even alternatively up to about 71° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound can be selected from the group consisting of fatty alcohols, fatty acids, and mixtures thereof. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are alternatively used in the composition of the present invention. The fatty alcohols can have from about 14 to about 30 carbon atoms, alternatively from about 16 to about 22 carbon atoms. These fatty alcohols are saturated and can be straight or branched chain alcohols.

Fatty alcohols can include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl, brassica or behenyl group.

The fatty alcohol can be a mixture of cetyl alcohol and stearyl alcohol.

Generally, in the mixture, the weight ratio of cetyl alcohol to stearyl alcohol is alternatively from about 1:9 to 9:1, alternatively from about 1:4 to about 4:1, alternatively from about 1:2.3 to about 1.5:1.

When using higher level of total cationic surfactant and high melting point fatty compounds, the mixture has the weight ratio of cetyl alcohol to stearyl alcohol of alternatively from about 1:1 to about 4:1, alternatively from about 1:1 to about 2:1, alternatively from about 1.2:1 to about 2:1, in view of avoiding to get too thick for spreadability. It may also provide more conditioning on damaged part of the hair.

Aqueous Carrier

The composition of the present invention can include an aqueous carrier. The level and species of the carrier can be selected according to the compatibility with other components, and other desired characteristic of the product.

The carrier can include water and water solutions of lower alkyl alcohols. The lower alkyl alcohols can be monohydric alcohols having 1 to 6 carbons, alternatively ethanol and isopropanol.

Alternatively, the aqueous carrier is substantially water. Deionized water is alternatively used. Water from natural sources including mineral cations can also be used, depending on the desired characteristic of the product. Generally, the compositions of the present invention comprise from about 40% to about 99%, alternatively from about 50% to about 95%, and alternatively from about 70% to about 93%, and alternatively from about 80% to about 92% water.

Gel Network

The gel network composition can be included in conditioner compositions to provide conditioning benefits, including improved wet feel of the hair after rinsing the conditioner. As used herein, the term "gel network" refers to a lamellar or vesicular solid crystalline phase which comprises at least one high melting point fatty compound, such as a fatty alcohol, as specified below, at least one surfactant, in particular a cationic surfactant, as specified below, and water or other suitable solvents. The lamellar or vesicular phase comprises bi-layers made up of a first layer comprising the high melting point fatty compound and the surfactant and alternating with a second layer comprising the water or other suitable solvent. Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International*, Vol. 7, 63-70 (1986).

A gel network can be formed by the cationic surfactant, the high melting point fatty compound, and an aqueous carrier. The gel network is suitable for providing various conditioning benefits, such as slippery feel during the application to wet hair and softness and moisturized feel on dry hair.

Alternatively, when the gel network is formed, the cationic surfactant and the high melting point fatty compound are contained at a level such that the weight ratio of the cationic surfactant to the high melting point fatty compound is in the range of, alternatively from about 1:1 to about 1:10, alternatively from about 1:1.5 to about 1:7, alternatively from about 1:2 to about 1:6, in view of providing improved wet conditioning benefits.

Alternatively, especially when the gel network is formed, the composition of the present invention is substantially free of anionic surfactants, in view of stability of the gel network. In the present invention, "the composition being substantially free of anionic surfactants" means that: the composition is free of anionic surfactants; or, if the composition contains anionic surfactants, the level of such anionic surfactants is very low. In the present invention, a total level of such anionic surfactants, if included, alternatively 1% or less, alternatively 0.5% or less, alternatively 0.1% or less by weight of the composition. Most alternatively, the total level of such anionic surfactants is 0% by weight of the composition.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, alternatively up to about 5% by weight of the composition.

A wide variety of other additional components can be formulated into the present compositions. These include: other conditioning agents such as aloe vera gel; aloe barbadensis leaf juice; ecklonia radiata extract; natural oils and waxes with shea butter, safflower oil, cocoa butter, orange peel wax, olive oil, macadamia seed oil, *Oenothera biennis* oil, *Crambe abyssinica* see oil, argon oil, camelina oil, sunflower oil, almond oil, *Argania spinosa* kernel oil, grape see oil, jojoba oil, coconut oil, meadowfoam seed oil, neem oil, linseed oil, castor oil, soybean oil, sesame oil, beeswax, sunflower wax, candelilla wax, rice bran wax, carnauba wax, bayberry wax and soy wax; essential oils such as lime peel oil, lavender oil, peppermint oil, cedarwood oil, tea tree oil, ylang-ylang oil and coensage oil which can be used in fragrance; hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; and ultraviolet and infrared screening and absorbing agents such as octyl salicylate; antioxidants include: rosemary, tocopherol, vitamin E, vitamin A, tea extracts, and hydroxyacetophenone (available as SymSave® H from Symrise®); amino acids include histidine, l-arginine and others.

Product Forms

The compositions of the present invention can be in the form of rinse-off products or leave-on products and can be formulated in a wide variety of product forms, including but not limited to creams, gels, emulsions, mousses, and sprays.

The conditioning composition of the present invention is especially suitable for rinse-off hair conditioner. Such compositions are alternatively used by following steps:
(i) after shampooing hair, applying to the hair an effective amount of the conditioning compositions for conditioning the hair; and
(ii) then rinsing the hair.

TEST METHODS

Bacterial Microbial Susceptibility Testing Method

Bacterial microbial susceptibility testing is used to assess the anti-bacterial effectiveness of the preservation system in cosmetic rinse-off conditioner.

A bacterial pool (mixture in equal volumes) of challenge organisms used in the test is comprised of standardized solutions of the bacterial strains *Escherichia coli* (ATCC #8739), *Staphylococcus aureus* (ATCC #6538), *Pseudomonas aeruginosa* (ATCC #9027), *Burkholderia cepacia* (ATCC #25416), as well as *Klebsiella pneumoniae, Enterobacter gergoviae* and *Serratia marcescens* strains isolated from cosmetic products. The bacterial pool is prepared to have a concentration of approximately 6-8 log cfu/ml. To start the test, 0.1 ml of the bacterial pool is added into 10.0 g of a test conditioner. The test conditioner is then incubated for 2 days at 20-25° C. After incubation, a 1.0 g aliquot of product is neutralized using Modified Letheen Broth containing 1.5% polysorbate 80 (commercially available as Tween® 80 from Croda™) and 1% Lecithin to aid in microbial recovery/enumeration. Then, multiple diluted concentrations of this sample are transferred into petri dishes containing Modified Letheen Agar with 1.5% Tween® 80, and the agar plates are incubated at least 2 days at 30-35° C. Bacterial colony forming units (cfus) are then enumerated, and a bacterial log reduction from the starting log cfu/g challenge level is reported.

A 1 log cfu/g reduction equates to ~a 90% bacterial reduction. A 2 log cfu/g reduction equates to ~a 99% bacterial reduction. A 3 log cfu/g reduction equates to ~a 99.9% bacterial reduction. A 4 log cfu/g reduction equates to ~a 99.99% bacterial reduction. Greater log cfu/g reduction values indicate greater antimicrobial robustness from the preservation system.

Fungal Microbial Susceptibility Testing Method:

Fungal microbial susceptibility testing is used to assess the anti-fungal effectiveness of the preservation system in cosmetic rinse-off conditioner.

Standardized ATCC strains of the yeast *Candida albicans* (ATCC #10231) and mold *Aspergillus brasiliensis* (frm. *niger*) (ATCC #16404) are mixed in 1:1 (v:v) ratio, and this fungal pool is used as inoculum in the test. The concentration of the fungal pool is approximately 6-8 log cfu/ml. To start the test, 0.1 ml of the fungal pool is added into 10.0 g of a testing conditioner. After the inoculated sample is incubated for 2 days at 20-25° C., a 1.0 g aliquot of product is neutralized using Modified Letheen Broth containing 1.5% Tween® 80 and 1% Lecithin to aid in microbial recovery/enumeration. Then, multiple diluted concentrations of this sample are transferred into petri dishes containing Modified Letheen Agar with 1.5% Tween 80, and the agar plates are incubated for at least 5 days at 20-25° C., at which time fungal colony forming units (cfus) are then enumerated, and a fungal log reduction from the starting log cfu/g challenge level is calculated.

A 1 log cfu/g reduction equates to ~a 90% fungal reduction. A 2 log cfu/g reduction equates to ~a 99% fungal reduction. A 3 log cfu/g reduction equates to ~a 99.9% fungal reduction. A 4 log cfu/g reduction equates to ~a 99.99% fungal reduction. Greater log cfu/g reduction values indicate greater anti-fungal robustness from the preservation system.

Differential Scanning calorimetry

The melt transition behavior and temperature for the gel network may be obtained using differential scanning calorimetry (DSC) according to the following method. Utilizing a TA Instruments Q2000 DSC, approximately 15 mg of the gel network pre-mix or the final conditioner composition containing the gel network is placed into a Tzero aluminum hermetic DSC pan. The sample, along with an empty reference pan is placed into the instrument. The samples are analyzed using the following conditions/temperature program: Nitrogen Purge at a rate of 50.0 mL/min; Equilibrate@20.00° C.; Sampling interval 0.10 sec/pt; Equilibrate at 5.00° C.; Isothermal for 1.00 min; Ramp 5.00° C./min to 80.00° C. The resulting DSC data is analyzed using TA Instruments Universal Analysis Software.

The use of DSC to measure the melt transition behavior and temperature for gel networks is further described by T. de Vringer et al., *Colloid and Polymer Science*, vol. 265, 448-457 (1987); and H. M. Ribeiro et al., *Intl. J. of Cosmetic Science*, vol. 26, 47-59 (2004).

pH Method

First, calibrate the Mettler Toledo Seven Compact pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 4 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 7 buffer and press the calibrate button a second time. Wait until the pH icon stops flashing and press the calibrate button a third time. Rinse the electrode with distilled water and carefully wipe the electrode with a scientific cleaning wipe. Then submerse the electrode into the pH 10 buffer and press the calibrate button a third time. Wait until the pH icon stops flashing and press the measure button. Rinse the electrode with distilled water and carefully wipe with a scientific cleaning wipe.

Submerse the electrode into the testing sample and press the read button. Wait until the pH icon stops flashing and record the value.

Shear Stress

Shear stress is measured by shear rate sweep condition with a rheometer available from TA Instruments with a mode name of ARG2. Geometry has 40 mm diameter, 2° C. cone angle, and gap of 49 μm. Shear rate is logarithmically increased from 0 to 1200/s for 1 min, and temperature is kept at 26.7° C. Share stress at a high shear rate of 950/s is measured and defined above.

X-Ray Diffraction Method

SAXS (Small Angle X-ray Scattering) is used to confirm the presence of a multi-lamellar phase, and WAXS (Wide Angle X-ray Scattering) is used to differentiate between Lα (liquid) and Lβ (solid) crystalline structures were employed to verify the presence of the characteristic dispersed gel network phase of the personal conditioning compositions d-Spacing (Lβ-Basal Spacing) of Lamella Gel Network:

Small-angle x-ray scattering ("SAXS") as used to resolve periodic structures in mesophases is essentially an x-ray diffraction technique. It is used in conjunction with conventional wide-angle x-ray scattering ("WAXS") to characterize aggregate structures such as micelles, gel networks, lamella, hexagonal and cubic liquid crystals. The different mesophases that show periodic structures can be characterized by the relative positions (d-spacing) of their reflections as derived from the Bragg equation ($d=\lambda/2 \sin\theta$) where d represents the interplanar spacing, $\lambda$ the radiation wavelength and $\theta$ the scattering (diffraction) angle.

The one dimensional lamella gel network phase is characterized by the ratio of the interplanar spacings $d_1/d_1$, $d_1/d_2$, $d_1/d_3$, $d_1/d_4$, $d_1/d_5$ having the values 1:2:3:4:5 etc. in the SAXS region (long-range order) and one or two invariant reflection(s) in the WAXS region (short-range) centered around 3.5 and 4.5 Å over a broad halo background. Other mesophases (e.g. hexagonal or cubic) will have characteristically different d-spacing ratios.

The SAXS data was collected with a Bruker NanoSTAR small-angle x-ray scattering instrument. The micro-focus Cu x-ray tube was operated at 50 kV, 0.60 mA with 550 um ScanTex Pinholes. The sample to detector distance was 107.39 cm and the detector a Vantec2K 2-dimensional area detector. Samples were sealed in capillaries and analyzed under vacuum with an analysis time of 600 s.

The value of d-spacing ((Lβ-basal spacing) of lamella gel network reported here is obtained with the $1^{st}$ order of SAXS reflection which is the $d_1$ spacing.

WAXS Confirmation (in Combination with SAXS) of Presence of Lβ Gel Network

Wide-angle data (WAXS) was collected on a Stoe STADI-MP diffractometer. The generator was operated at 40 kV/40 mA, powering a copper anode long-fine-focus Cu x-ray tube. The diffractometer incorporates an incident-beam curved germanium-crystal monochromator, standard incident-beam slit system, and Mythen PSD detector. Data were collected in transmission mode over a range of 0° to 50° 2θ with a step size of 3° 2θ and 15 seconds per step.

WAXS Pattern with reflection near 4.2 Å which, in combination with the lamellar reflections seen in the SAXS, is indicative of the presence of LP gel network.

EXAMPLES

The following are non-limiting examples of the conditioner compositions described herein. It will be appreciated that other modifications of the present invention within the skill of those in the art can be undertaken without departing from the spirit and scope of this invention.

All parts, percentages, and ratios herein are by weight unless otherwise specified. Some components may come from suppliers as dilute solutions. The amount stated reflects the weight percent of the added material, unless otherwise specified.

The examples in Table 2 to Table 11 were made as follows. Sodium benzoate and l-glutamic were dissolved in the water. The mixture was heated to 80° C. Then, the cationic surfactant and fatty alcohols (FAOH) were added to the mixture. Next, the mixture was cooled while the cationic surfactant and fatty alcohols continue to dissolve. Then, the additional preservatives were added followed by oils and perfume when the temperature was below 45° C. The composition was cooled to room temperature to make the conditioner composition.

Table 2, below, shows Comparative Examples 1-4. Even though these compositions contain an effective surfactant system that that is EWG VERIFIED™, does not contain any of the ingredients that Whole Foods® Market lists as unacceptable, and is categorized as "risk-free" by the Yuka® Application, they are not consumer preferred.

TABLE 2

Comparative Examples 1-2

|  | Comp. Ex. 1 | Comp. Ex. 2 | Comp. Ex. 3 | Comp. Ex. 4 |
|---|---|---|---|---|
| Sheer stress (Pa) @950 1/s | 60 | 65 | 354 | 299 |
| DSC peak (melting temp) | 2 peaks | 2 peaks | 2 peaks | 2 peaks |
| Behenamidopropyl Dimethylamine (BAPDMA) wt % (active)[1] | 6.74 | 7.48 | 2.25 | 1.50 |
| ℓ-Glutamic Acid wt % (active)[2] | 2.78 | 3.09 | 0.93 | 0.62 |
| Cetyl Alcohol (C16 Fatty alcohol) wt % (active)[3] | 2.81 | 2.55 | 4.34 | 4.59 |
| Stearyl Alcohol (C18 Fatty Alcohol) wt % (active)[4] | 2.09 | 1.90 | 3.23 | 3.42 |
| Sodium Benzoate wt % (active)[5] | 0.20 | 0.20 | 0.20 | 0.20 |
| Caprylyl Glycol wt % (active)6 | 0.40 | 0.40 | 0.40 | 0.40 |
| Distilled Water | Q.S. | Q.S. | Q.S. | Q.S. |
| Citric Acid | Adjust pH to 3.5-4.5 | | | |
| Total GN content (BAPDMA + FAOH molar) | 0.351 | 0.351 | 0.351 | 0.351 |
| C18 FAOH/total FAOH (molar) | 0.40 | 0.40 | 0.40 | 0.40 |
| ℓ-Glutamic acid to BAPDMA molar ratio | 1.24 | 1.25 | 1.25 | 1.25 |
| Molar ratio of BAPDMA to FAOH | 45:55 | 50:50 | 15:85 | 10:90 |

Comparative Examples 1-4 all have two peaks, according to the Differential Scanning calorimetry Test Method, which indicates that the gel network is non-uniform and may provide poor conditioning, a poor user experience, and/or instability including a short shelf life. FIG. 2 shows the melt transition behavior of the gel network of select examples: Examples 1-5 (see Table 3, below) and Comparative Examples 1 and 2. The curves were made according to the Differential Scanning calorimetry Test Method, described herein. The DSC curve for Comparative Examples 1 and 2 all show two peaks.

In Comparative Examples 1-2, the molar ratio of BAPDMA to fatty alcohol is too high and since there is an excess of BAPDMA, you do not form the correct gel network that provides good conditioning and shear stress to form a consumer acceptable product.

In Comparative Examples 3-4, the molar ratio BADPMA to fatty alcohol is too low and since there is too little BADPMA not enough fatty alcohol was incorporated into the gel network. These examples have a poor gel network that does not provide good conditioning. Also, the excess of fatty alcohol can leave a greasy or weighed down feeling to the hair because too much fatty alcohol is deposited on the hair.

Table 3 to Table 8, below, show Examples 1-35, which are consumer acceptable conditioner compositions. The uniform conditioner compositions in Table 3 to Table 8 contain an effective surfactant system that that is EWG VERIFIED™, does not contain any of the ingredients that Whole Foods® Market lists as unacceptable, and is categorized as "risk-free" by the Yuka® Application.

TABLE 3

Examples 1-6

|  | Ex. 1 | Ex. 2 | Ex. 3 | Ex. 4 | Ex. 5 | Ex. 6 |
|---|---|---|---|---|---|---|
| Sheer stress (Pa) @950 1/s | 278 | 334 | 345 | 160 | 107 | 270 |
| DSC peak (melting temp) | 1 peak | 1 peak | 1 peak | 1 peak | 1 peak | 1 peak |
| GN d-spacing (nm) | 24.8 | 20.8 | 23.9 | 22.8 | 21.2 | 26.8 |
| Behenamidopropyl Dimethylamine (BAPDMA) wt % (active)[1] | 2.99 | 3.74 | 4.50 | 5.24 | 5.99 | 2.99 |
| ℓ-Glutamic Acid wt % (active)[2] | 1.24 | 1.05 | 1.86 | 2.16 | 2.47 | 0.83 |
| Cetyl Alcohol (C16 Fatty alcohol) wt % (active)[3] | 4.08 | 3.83 | 3.57 | 3.31 | 3.06 | — |
| Stearyl Alcohol (C18 Fatty Alcohol) wt % (active)[4] | 3.03 | 2.84 | 2.66 | 2.46 | 2.28 | — |
| Brassical Alcohol (C21 Fatty Alcohol) wt %[7] | — | — | — | — | — | 8.77 |
| Sodium Benzoate wt % (active)[5] | 0.20 | 0.20 | 0.20 | 0.20 | 0.20 | 0.20 |
| Benzyl Alcohol wt % (active)[8] | — | — | — | — | — | 0.40 |
| Shea Butter wt % (active)[9] | 0.50 | 0.50 | 0.50 | 0.50 | 0.50 | 0.50 |
| Perfume | 0.65 | 0.65 | 0.65 | 0.65 | 0.65 | 0.65 |
| Distilled Water | Q.S. | Q.S. | Q.S. | Q.S. | Q.S. | Q.S. |
| Citric Acid | Adjust pH to 3.5-4.5 | | | | | |
| Total GN content (BAPDMA + FAOH molar) | 0.351 | 0.351 | 0.351 | 0.351 | 0.351 | 0.351 |
| C18OH/total FAOH (molar) | 0.40 | 0.40 | 0.40 | 0.40 | 0.40 | — |
| ℓ-Glutamic acid to BAPDMA molar ratio | 1.25 | 0.85 | 1.25 | 1.24 | 1.24 | 0.84 |
| Molar ratio of BAPDMA to FAOH | 20:80 | 25:75 | 30:70 | 35:65 | 40:60 | 20:80 |

TABLE 4

Examples 7-12

| | Ex. 7 | Ex. 8 | Ex. 9 | Ex. 10 | Ex. 11 | Ex. 12 |
|---|---|---|---|---|---|---|
| Sheer stress (Pa) @950 1/s | 249 | 233 | 141 | 516 | 562 | 338 |
| DSC peak (melting temp) | 1 peak | 1 peak | 1 peak | 1 peak | 1 peak | 1 peak |
| GN d-spacing (nm) | 25.8 | 24.2 | 24.4 | 21.6 | 21.5 | 22 |
| Behenamidopropyl Dimethylamine (BAPDMA) wt % (active)[1] | 3.12 | 3.74 | 4.37 | 4.68 | 4.68 | 5.61 |
| ℓ-Glutamic Acid wt % (active)[2] | 0.87 | 1.22 | 1.22 | 1.95 | 1.95 | 1.95 |
| Cetyl Alcohol (C16 Fatty alcohol) wt % (active)[3] | 1.60 | 1.49 | 1.81 | 4.78 | 4.78 | 4.46 |
| Stearyl Alcohol (C18 Fatty Alcohol) wt % (active)[4] | 4.15 | 3.87 | 3.12 | 3.56 | 3.56 | 3.32 |
| Sodium Benzoate wt % (active)[5] | 0.20 | 0.20 | 0.20 | 0.20 | 0.20 | 0.20 |
| Benzyl Alcohol wt % (active)[7] | 0.40 | 0.40 | 0.40 | — | — | — |
| Shea Butter wt % (active)[9] | 0.50 | 0.50 | 0.50 | 2.00 | 0.50 | 0.50 |
| Safflower oil wt % (active)[10] | — | — | — | — | 0.55 | 0.55 |
| Argon oil wt % (active)[11] | — | — | — | 1.50 | — | — |
| jojoba oil wt % (active)[12] | — | — | — | 1.50 | — | — |
| Perfume | 0.65 | 0.65 | 0.65 | 0.65 | 0.65 | 0.65 |
| Distilled Water | Q.S. | Q.S. | Q.S. | Q.S. | Q.S. | Q.S. |
| Citric Acid | | | Adjust pH to 3.5-4.5 | | | |
| Total GN content (BAPDMA + FAOH molar) | 0.293 | 0.293 | 0.293 | 0.439 | 0.439 | 0.439 |
| C18 FAOH/total FAOH (molar) | 0.70 | 0.70 | 0.70 | 0.40 | 0.40 | 0.40 |
| ℓ-Glutamic acid to BAPDMA molar ratio | 0.84 | 0.98 | 0.84 | 1.26 | 1.26 | 1.05 |
| Molar ratio of BAPDMA to FAOH | 25:75 | 30:70 | 35:65 | 25:75 | 25:75 | 30:70 |

TABLE 5

Examples 13-18

| | Ex. 13 | Ex. 14 | Ex. 15 | Ex. 16 | Ex. 17 | Ex. 18 |
|---|---|---|---|---|---|---|
| Sheer stress (Pa) @950 1/s | 456 | 290 | 158 | 174 | 276 | 275 |
| DSC peak (melting temp) | 1 peak | 1 peak | 1 peak | 1 peak | 1 peak | 1 peak |
| GN d-spacing (nm) | 21.5 | 25.4 | 24.2 | 26.2 | 24.9 | 23.5 |
| Behenamidopropyl Dimethylamine (BAPDMA) wt % (active)[1] | 4.21 | 3.74 | 3.74 | 3.74 | 3.74 | 3.74 |
| ℓ-Glutamic Acid wt % (active)[2] | 1.75 | 1.55 | 1.55 | 1.05 | 1.05 | 1.05 |
| Cetyl Alcohol (C16 Fatty alcohol) wt % (active)[3] | 4.30 | 3.83 | 3.83 | 3.83 | 1.91 | 1.91 |
| Stearyl Alcohol (C18 Fatty Alcohol) wt % (active)[4] | 3.20 | 2.84 | 2.84 | 2.84 | 4.99 | 4.99 |
| Sodium Benzoate wt % (active)[5] | 0.20 | 0.20 | 0.20 | 0.20 | 0.20 | 0.20 |
| Caprylyl Glycol wt % (active)[6] | — | — | 0.40 | 0.40 | — | — |
| Benzyl Alcohol wt % (active)[7] | — | — | — | — | — | 0.40 |
| Shea Butter wt % (active)[9] | 0.50 | 2.00 | 0.50 | 0.50 | 0.50 | 0.50 |
| Safflower oil wt % (active)[10] | 0.55 | — | — | — | — | — |
| Argon oil wt % (active)[11] | — | 1.50 | — | — | — | — |
| jojoba oil wt % (active)[12] | — | 1.50 | — | — | — | — |
| Perfume | 0.65 | 0.65 | 0.65 | 0.65 | 0.65 | 0.65 |
| Distilled Water | Q.S. | Q.S. | Q.S. | Q.S. | Q.S. | Q.S. |
| Citric Acid | | | Adjust pH to 3.5-4.5 | | | |
| Total GN content (BAPDMA + FAOH molar) | 0.395 | 0.351 | 0.351 | 0.351 | 0.351 | 0.351 |
| C18 FAOH/total FAOH (molar) | 0.40 | 0.40 | 0.40 | 0.40 | 0.70 | 0.70 |
| ℓ-Glutamic acid to BAPDMA molar ratio | 1.25 | 1.25 | 1.25 | 0.85 | 0.85 | 0.85 |

TABLE 5-continued

Examples 13-18

| | Ex. 13 | Ex. 14 | Ex. 15 | Ex. 16 | Ex. 17 | Ex. 18 |
|---|---|---|---|---|---|---|
| Molar ratio of BAPDMA to FAOH | 25:75 | 25:75 | 25:75 | 25:75 | 25:75 | 25:75 |

TABLE 6

Examples 19-24

| | Ex. 19 | Ex. 20 | Ex. 21 | Ex. 22 | Ex. 23 | Ex. 24 |
|---|---|---|---|---|---|---|
| Sheer stress (Pa) @950 1/s | 303 | 261 | 178 | 231 | 170 | 160 |
| DSC peak (melting temp) | 1 peak | 1 peak | 1 peak | 1 peak | 1 peak | 1 peak |
| GN d-spacing (nm) | 21.9 | 23.1 | 23.1 | 22.7 | 23.1 | 22.8 |
| Behenamidopropyl Dimethylamine (BAPDMA) wt % (active)[1] | 4.50 | 4.50 | 4.50 | 5.24 | 5.24 | 5.24 |
| ℓ-Glutamic Acid wt % (active)[2] | 1.86 | 1.25 | 1.25 | 1.46 | 1.46 | 1.46 |
| Cetyl Alcohol (C16 Fatty alcohol) wt % (active)[3] | 1.79 | 1.70 | 1.79 | 3.32 | 1.66 | 1.66 |
| Stearyl Alcohol (C18 Fatty Alcohol) wt % (active)[4] | 4.65 | 4.51 | 4.65 | 2.46 | 4.32 | 4.32 |
| Sodium Benzoate wt % (active)[5] | 0.20 | 0.20 | 0.20 | 0.20 | 0.20 | 0.20 |
| Caprylyl Glycol wt % (active)[6] | — | — | 0.40 | — | — | — |
| Benzyl Alcohol wt % (active)[7] | — | 0.40 | — | 0.40 | — | 0.40 |
| Shea Butter wt % (active)[9] | 0.50 | 0.50 | 0.50 | 0.50 | 0.50 | 0.50 |
| Perfume | 0.65 | 0.65 | 0.65 | 0.65 | 0.65 | 0.65 |
| Distilled Water | Q.S. | Q.S. | Q.S. | Q.S. | Q.S. | Q.S. |
| Citric Acid | Adjust pH to 3.5-4.5 | | | | | |
| Total GN content (BAPDMA + FAOH molar) | 0.351 | 0.351 | 0.351 | 0.351 | 0.351 | 0.351 |
| C18 FAOH/total FAOH (molar) | 0.70 | 0.70 | 0.70 | 0.40 | 0.70 | 0.70 |
| ℓ-Glutamic acid to BAPDMA molar ratio | 1.25 | 0.84 | 0.84 | 0.84 | 0.84 | 0.84 |
| Molar ratio of BAPDMA to FAOH | 30:70 | 30:70 | 30:70 | 20:101 | 20:102 | 20:103 |

TABLE 7

Examples 25-28

| | Ex. 25 | Ex. 26 | Ex. 27 | Ex. 28 |
|---|---|---|---|---|
| Sheer stress (Pa) @950 1/s | 258 | 283 | 287 | 300 |
| DSC peak (melting temp) | 1 peak | 1 peak | 1 peak | 1 peak |
| GN d-spacing (nm) | 23.2 | 21.2 | 23.1 | 22.3 |
| Behenamidopropyl Dimethylamine (BAPDMA) wt % (active)[1] | 3.74 | 3.74 | 3.74 | 3.74 |
| ℓ-Glutamic Acid wt % (active)[2] | 1.55 | 1.55 | 1.55 | 1.55 |
| Cetyl Alcohol (C16 Fatty alcohol) wt % (active)[3] | 3.83 | 3.83 | 3.83 | 3.83 |
| Stearyl Alcohol (C18 Fatty Alcohol) wt % (active)[4] | 2.84 | 2.84 | 2.84 | 2.84 |
| Sodium Benzoate wt % (active)[5] | 0.20 | 0.20 | 0.20 | 0.20 |
| Shea Butter wt % (active)[9] | 0.50 | 0.50 | — | — |
| Safflower oil wt % (active)[10] | — | 0.55 | 2.00 | — |
| Histidine wt % (active)[13] | 0.01 | 0.01 | 0.01 | 0.01 |
| Aloe Barbadensis Leaf Juice wt % (active)[14] | 0.05 | 0.05 | 0.05 | 0.05 |
| Ecklonia Radiata Extract wt % (active)[15] | 0.02 | 0.02 | 0.02 | 0.02 |
| Perfume | 0.65 | 0.65 | 0.65 | 0.40 |
| Distilled Water | Q.S. | Q.S. | Q.S. | Q.S. |
| Citric Acid | Adjust pH to 3.5-4.5 | | | |
| Total GN content (BAPDMA + FAOH molar) | 0.351 | 0.351 | 0.351 | 0.351 |
| C18 FAOH/total FAOH (molar) | 0.40 | 0.40 | 0.40 | 0.40 |
| ℓ-Glutamic acid to BAPDMA molar ratio | 1.25 | 1.25 | 1.25 | 1.25 |
| Molar ratio of BAPDMA to FAOH | 25:75 | 25:75 | 25:75 | 25:75 |

TABLE 8

Examples 29-35

|  | Ex. 29 | Ex. 30 | Ex. 31 | Ex. 32 | Ex. 33 | Ex. 34 | Ex. 35 |
|---|---|---|---|---|---|---|---|
| Sheer stress (Pa) @950 1/s | 306 | 312 | 150 | 172 | 117 | 118 | 198 |
| Behenamidopropyl Dimethylamine (BAPDMA) wt % (active)[1] | 3.74 | 3.74 | 3.72 | 3.72 | 3.27 | 3.27 | 2.81 |
| ℓ-Glutamic Acid wt % (active)[2] | 1.55 | 1.55 | 1.50 | 1.55 | 0.91 | 0.91 | 0.78 |
| Cetyl Alcohol (C16 Fatty alcohol) wt % (active)[3] | 3.83 | 3.83 | 1.50 | 2.47 | 1.26 | 2.53 | 1.36 |
| Stearyl Alcohol (C18 Fatty Alcohol) wt % (active)[4] | 2.84 | 2.84 | 2.86 | 1.80 | 2.45 | 1.33 | 2.64 |
| Sodium Benzoate wt % (active)[5] | 0.2 | 0.25 | 0.25 | 0.25 | 0.25 | 0.25 | 0.25 |
| Caprylyl Glycol wt % (active)[6] | 0.40 | 0.40 | 0.40 | 0.40 | 0.40 | 0.40 | 0.40 |
| Histidine wt % (active)[13] | 0.01 | 0.01 | 0.01 | 0.01 | 0.01 | 0.01 | 0.01 |
| Aloe Barbadensis Leaf Juice wt % (active)[14] | 0.05 | 0.05 | 0.05 | 0.05 | 0.05 | 0.05 | 0.05 |
| Ecklonia Radiata Extract wt % (active)[15] | 0.02 | 0.02 | 0.02 | 0.02 | 0.02 | 0.02 | 0.02 |
| Perfume | 0.40 | 0.40 | 0.40 | 0.40 | 0.40 | 0.40 | 0.40 |
| Distilled Water | Q.S. | Q.S. | Q.S. | Q.S. | Q.S. | Q.S. | Q.S. |
| Citric Acid | | | Adjust pH to 3.5-4.5 | | | | |
| Total molar content of BAPDMA + FAOH | 0.351 | 0.351 | 0.249 | 0.249 | 0.220 | 0.220 | 0.220 |
| C18 FAOH/total FAOH (molar) | 0.40 | 0.40 | 0.70 | 0.40 | 0.70 | 0.40 | 0.70 |
| ℓ-Glutamic acid to BAPDMA molar ratio | 1.25 | 1.25 | 1.22 | 1.26 | 0.84 | 0.84 | 0.84 |
| Molar ratio of BAPDMA to FAOH | 25:75 | 25:75 | 35:65 | 35:65 | 35:65 | 35:65 | 30:70 |

Suppliers for Examples in Table 2 to Table 8
1. Behenamidopropyl Dimethylamine (BAPDMA) (Incromine™ BD), available from Croda®
2. l-Glutamic Acid, available from Ajinomoto®
3. Cetyl alcohol, 95% active level available from Procter & Gamble®
4. Stearyl alcohol, 97% active level, available from Procter & Gamble®
5. Sodium Benzoate, available from Kalama®
6. Caprylyl Glycol, available from Procter and Gamble®
7. Brassical Alcohol (SustOleo™ BA), available from Inolex®
8. Benzyl Alcohol, available form Charkit®
9. Shea Butter, available form Procter and Gamble®
10. Safflower oil (*Carthamus tinctorius* seed oil), available from Southern Cross Botanicals
11. Argon oil (*Argania spinosa* kernel oil), available from BASF®
12. Jojoba oil (*Simmondsia chinensis* seed oil), available from Southern Cross Botanicals
13. Histidine (L-Histidine), available from Ajinomoto®
14. Aloe Barbadensis Leaf Juice, available form Procter and Gamble®
15. Ecklonia Radiata Extract (Australian See Kelp Extract), available from Southern Cross Botanicals Examples 1-35 all have one melting transition peak, according to the Differential Scanning calorimetry Test Method, described herein, which indicates that the gel network is uniform and the may provide good conditioning performance, a good user experience, and may be stable. FIG. 2 shows the melt transition behavior of the gel network of Examples 1-5 (Table 3) and each curve for Examples 1-5 has only one peak. As shown in FIG. 2, Examples 1-5, one peak can be a single distinct peak, or it can be merged set of peaks. However, Comparative Example 2 (Table 2) has more than one peak, which can indicate that the gel network is not uniform.

The shear stress is consumer acceptable and ranges from 107 Pa to 562 Pa, if the shear stress is too low or too high it can be difficult for a consumer to apply the conditioner composition throughout their hair with their hands. If the shear stress is too low, the conditioner composition can drip from the hand and hair and if the shear stress is too high, it can be difficult to spread.

The gel network d-spacing is from 20.8 to 26.9 for Examples 1-28. This level of d-spacing indicates that the conditioner composition can provide good conditioning with good wet feel and good wet detangling.

Examples 1-35 have a molar ratio of BAPDMA to FAOH of greater than or equal to 20:80 and less than or equal to 40:60. It was surprisingly found that if the molar ratio of BAPDMA to FAOH was in this range and the conditioner contains sodium benzoate then the conditioner composition had a gel network with d-spacing that indicates good wet conditioning performance was formed. It is believed that other salts, including sodium salicylate, sodium chloride, sodium carbonate, sodium borate, sodium acetate, sodium citrate, potassium benzoate, potassium acetate, calcium gluconate, calcium chloride, and potassium sorbate, would form a gel network with the proper d-spacing was formed.

In Table 9 to Table 11, below, the Micro-Bacteria@2 days and the Micro-Fungi@2 days is determined by the Bacterial and Fungal Microbial Susceptibility Test Methods, described herein. For the preservation system to be effective, the level of microbes (bacteria and fungi) needs to be undetectable, which means that there is a greater than 99.99% reduction in microbes at two days as determined by the Bacterial and Fungal Microbial Susceptibility Test Methods. In Table 10, below, N/A indicates that the test was not performed.

TABLE 9

Comp. Examples A-F

| | Comp. Ex. A | Comp. Ex. B | Comp. Ex. C | Comp. Ex. D | Comp. Ex. E | Comp. Ex. F |
|---|---|---|---|---|---|---|
| Appearance | Creamy and smooth | | | | | |
| Sheer stress (Pa) @950 1/s | 350 | 419 | 448 | 450 | 354 | 343 |
| Micro-Bacteria @ 2 days | ~90% reduction | Not Detectable (>99.99% reduction) | | | | |
| Micro-Fungi @ 2 days | | ~90% reduction | | | >99% reduction | |
| Sodium Benzoate wt % (active)[1] | — | 0.20 | 0.25 | 0.40 | 0.20 | 0.25 |
| Caprylyl Glycol wt % (active)[2] | — | — | — | — | 0.20 | 0.20 |
| Behenamidopropyl Dimethylamine (Cationic Surfactant) wt % (active)[6] | 3.74 | 3.74 | 3.74 | 3.74 | 3.74 | 3.74 |
| ℓ-Glutamic Acid wt % (active)[7] | 1.55 | 1.55 | 1.55 | 1.55 | 1.55 | 1.55 |
| Cetyl Alcohol (C16 Fatty alcohol) wt % (active)[8] | 3.83 | 3.83 | 3.83 | 3.83 | 3.83 | 3.83 |
| Stearyl Alcohol (C18 Fatty Alcohol) wt % (active)[9] | 2.84 | 2.84 | 2.84 | 2.84 | 2.84 | 2.84 |
| Citric Acid wt % | 0.25 | 0.25 | 0.35 | 0.25 | 0.25 | 0.35 |
| Distilled Water | Q.S. | Q.S. | Q.S. | Q.S. | Q.S. | Q.S. |
| pH | 3.9 | 4.2 | 4.2 | 4.3 | 4.2 | 4.2 |

TABLE 10

Comparative Examples G-K

| | Comp. Ex. G | Comp. Ex. H | Comp. Ex. I | Comp. Ex. J | Comp. Ex. K |
|---|---|---|---|---|---|
| Appearance | Creamy and smooth | | | Clumpy and grainy | Thin and grainy |
| Sheer stress (Pa) @950 1/s | 270 | 275 | 271 | N/A | |
| Micro-Bacteria @ 2 day | Not Detectable (>99.99% reduction) | | | N/A | |
| Micro-Fungi @ 2 days | >90% reduction | | >99% reduction | N/A | |
| Sodium Benzoate wt % (active)[1] | 0.20 | 0.20 | 0.20 | 1.00 | — |
| Caprylyl Glycol wt % (active)[2] | — | — | — | — | 2.00 |
| Glyceryl Caprylate/Caprate wt % (active)[3] | 0.40 | — | — | — | — |
| Glyceryl Caprylate (and) Glyceryl Undecylenate wt % (active)[4] | — | 0.40 | — | — | — |
| Behentrimonium Chloride (Cationic Surfactant) wt % (active)[5] | — | — | 2.28 | — | — |
| Behenamidopropyl Dimethylamine (cationic surfactant) wt % (active)[6] | 3.74 | 3.74 | — | 3.74 | 3.74 |
| ℓ-Glutamic Acid wt % (active)[7] | 1.55 | 1.55 | — | 1.55 | 1.55 |
| Cetyl Alcohol (C16 Fatty alcohol) wt % (active)[8] | 3.83 | 3.83 | 1.67 | 3.83 | 3.83 |
| Stearyl Alcohol (C18 Fatty Alcohol) wt % (active)[9] | 2.84 | 2.84 | 4.50 | 2.84 | 2.84 |
| Citric Acid | 0.25 | 0.25 | 0.035 | 1.25 | 0.25 |
| Distilled Water | Q.S. | Q.S. | Q.S. | Q.S. | Q.S. |
| pH | 4 | 4.1 | 4.4 | 4 | 4.1 |

Comparative Example A is the control and does not contain a preservation system. Comparative Example A does not provide enough microbe reduction at 2 days for bacteria and fungi.

Comparative Examples B, C, and D contain 0.20 wt %, 0.25 wt %, and 0.40 wt % sodium benzoate, respectively, and these examples have an undetectable level (>99.99% reduction) of bacteria at two days. However, a preservation system that contains only sodium benzoate at these levels does not provide enough fungi reduction at two days, as these examples only have a ~90% reduction.

Comparative Examples E and F include a preservation system that has both sodium benzoate and caprylyl glycol. These examples have an undetectable level (>99.99% reduction) of bacteria at two days. The combination of sodium benzoate and caprylyl glycol improves the reduction of fungi at 2 days, as compared to Comparative Examples B, C, and D. However, there is still a detectable level of fungi and therefore the preservation system in these examples is not considered effective.

Comparative Example G has a preservation system with 0.20 wt % sodium benzoate and 0.40 wt % glyceryl caprylate/caprate (a glyceryl ester) and this example has an undetectable level (>99.99% reduction) of bacteria at two days. However, it has a >90% reduction in fungi at two days and is ineffective.

Similar to Comparative Example GG, Comparative Example H has a preservation system with 0.20 wt % sodium benzoate and 0.40 wt % glyceryl caprylate (and) glyceryl undeylenate and this example has an undetectable level (>99.99% reduction) of bacteria at two days. However, it has a >90% reduction in fungi at two days and is ineffective.

Comparative Example I contains 0.20% sodium benzoate and behentrimonium chloride (cationic surfactant) and this example has an undetectable level (>99.99% reduction) of bacteria at two days. However, it has a detectable level of fungi (>99% reduction) at two days and is therefore ineffective.

Figure 3:
FIG. 3 is a photograph of the conditioner composition of Comparative Example J, which contains 1 wt % sodium benzoate and has a clumpy and grainy appearance.

Comparative Example J contains 1 wt % sodium benzoate. As shown in FIG. 3, instead of being a smooth, creamy conditioner, it was clumpy and grainy, which is not consumer preferred. While not willing to be bound by theory, it is believed that the sodium benzoate level in this example is too high and since sodium benzoate is a salt, it effects the packing of the gel network. For example, in this example it is believed that some regions the gel network may be packed too tight and this can lead to the clumpy texture.

Figure 4:
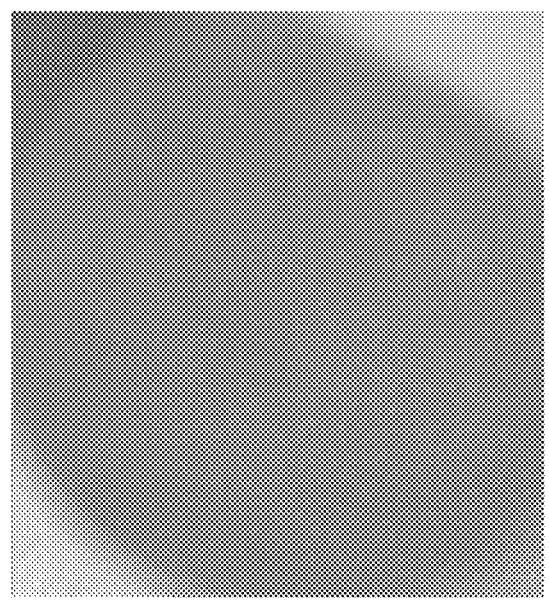
FIG. 4 is a photograph of the conditioner composition of Comparative Example K, which contains 2 wt % sodium benzoate and has a thin and grainy appearance.

Comparative Example K contains 2 wt % caprylyl glycol. As shown in FIG. 4, instead of being a smooth, creamy conditioner, it was thin and crystalline appearance. A conditioner with this texture could be difficult for a consumer to apply with their hands and may not provide good conditioning. While not willing to be bound by theory, it is believed that if the level of glycol is too high, it acts like a solvent and breaks down the gel network.

TABLE 11

Examples A-E

| | Ex. A | Ex. B | Ex. C | Ex. D | Ex. E |
|---|---|---|---|---|---|
| Appearance | Creamy and smooth | | | | |
| Sheer stress (Pa) @950 1/s | 304 | 302 | 289 | 290 | 141 |
| Micro-Bacteria @ 2 days | Not Detectable (>99.99% reduction) | | | | |
| Micro-Fungi @ 2 days | Not Detectable (>99.99% reduction) | | | | |
| Sodium Benzoate wt % (active)[1] | 0.20 | 0.25 | 0.40 | 0.40 | 0.20 |
| Caprylyl Glycol wt % (active)[2] | 0.40 | 0.40 | — | — | 0.40 |
| Glyceryl Caprylate/Caprate wt % (active)[3] | — | — | 0.40 | — | — |
| Glyceryl Caprylate (and) Glyceryl Undecylenate wt % (active)[4] | — | — | — | 0.40 | — |
| Behentrimonium Chloride (Cationic Surfactant) wt % (active)[5] | — | — | — | — | 2.28 |
| Behenamidopropyl Dimethylamine (Cationic Surfactant) wt % (active)[6] | 3.74 | 3.74 | 3.74 | 3.74 | — |
| ℓ-Glutamic Acid wt % (active)[7] | 1.55 | 1.55 | 1.55 | 1.55 | — |
| Cetyl Alcohol (C16 Fatty alcohol) wt % (active)[8] | 3.83 | 3.83 | 3.83 | 3.83 | 1.67 |
| Stearyl Alcohol (C18 Fatty Alcohol) wt % (active)[9] | 2.84 | 2.84 | 2.84 | 2.84 | 4.50 |
| Citric Acid | 0.25 | 0.35 | 0.25 | 0.25 | 0.035 |
| Distilled Water | Q.S. | Q.S. | Q.S. | Q.S. | Q.S. |
| pH | 4.2 | 4.2 | 4.1 | 4.1 | 4.4 |

Suppliers for Examples in Table 9 to Table 11
1. Sodium Benzoate, available from Kalama®
2. Caprylyl Glycol, available from Procter and Gamble®
3. Glyceryl Caprylate/Caprate (STEPAN-MILD® GCC), available from Stepan®
4. Glyceryl Caprylate (and) Glyceryl Undecylenate (Lexgard® Natural), available from Inolex®
5. Behentrimonium Chloride/IPA (Genamin KDMP), available from Clariant™ at 80% active level
6. Behenamidopropyl Dimethylamine (BAPDMA) (Incromine™ BD), available from Croda®
7. l-Glutamic Acid, available from Ajinomoto®
8. Cetyl alcohol, 95% active level available from Procter & Gamble®
9. Stearyl alcohol, 97% active level, available from Procter & Gamble®

Figure 5:
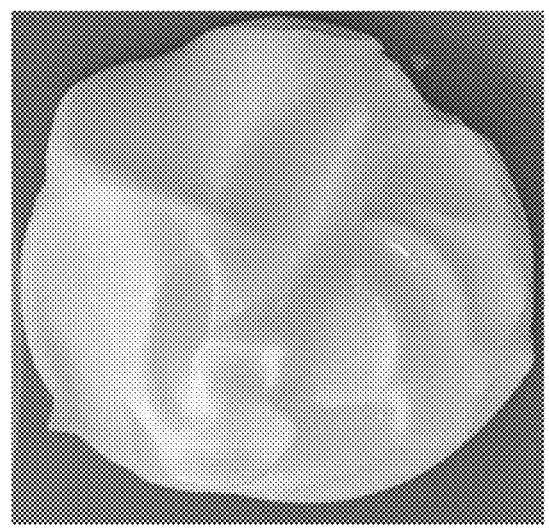
FIG. 5 is a photograph of the conditioner composition of Example A, which contains 0.20 wt % sodium benzoate and 0.40 wt % caprylyl glycol.

All of the Examples in Table 11 have preservation systems that are effective (i.e. bacteria and fungi are not detectable (>99.99% reduction) at 2 days) and a creamy and smooth appearance that is consumer preferred. FIG. 5 is a photograph of Example A that shows the smooth and creamy appearance of the conditioner composition. These examples have between 0.20-0.40 wt % sodium benzoate and 0.40 wt % caprylyl glycol, glyceryl caprylate/caprate, or glyceryl caprylate (and) glyceryl undecylenate. The weight ratio of sodium benzoate to caprylyl glycol, glyceryl caprylate/caprate, or glyceryl caprylate (and) glyceryl undecylenate is from about 1:2 to about 1:1.

All the Examples in Table 11 have a creamy and smooth appearance that can be consumer preferred.

Combinations:
A. A hair conditioner composition comprising:
   a. an aqueous carrier;
   b. behenamidopropyl dimethylamine (BAPDMA);
   c. a fatty alcohol;
   d. a salt selected from the group consisting of sodium benzoate, sodium salicylate, sodium chloride, sodium carbonate, sodium borate, sodium acetate, sodium citrate, potassium benzoate, potassium acetate, calcium gluconate, calcium chloride, potassium sorbate, and combinations thereof;
   wherein the molar ratio of behenamidopropyl dimethylamine to fatty alcohol is from about 3:25 to about 9:10, preferably from about 7:50 to about 4:5, more preferably from about 3:20 to about 3:4, even more preferably from about 17:100 to about 7:10, and even more preferably from about 9:50 to about 2:3;
   wherein the composition comprises a uniform gel network;
   wherein the composition comprises d-spacing of less than 32 nm, as measured according to the d-spacing (Lβ-basal spacing) of Lamella Gel Network Test Method, described herein.

B. The hair conditioner composition of Paragraph A, further comprising an acid selected from the group consisting l-glutamic acid, lactic acid, hydrochloric acid, malic acid, succinic acid, acetic acid, fumaric acid, tartaric acid, citric acid, l-glutamic hydrochloride, maleic acid, and mixtures thereof.

C. The hair conditioner composition of Paragraph B, wherein the conditioner composition comprises from about 0.25 wt % to about 6 wt % acid, preferably from about 0.4 wt % to about 5 wt % acid, more preferably from about 0.5 wt % to about 4 wt % acid, and even more preferably from about 0.6 wt % to about 3 wt % acid.

D. The hair conditioner composition of Paragraphs A-C, wherein the composition comprises less than 2 wt % salt, preferably less than 1.5 wt % salt, more preferably less than 1 wt % salt, even more preferably less than 0.8 wt % salt, even more preferably less than 0.6 wt % salt, and even more preferably less than 0.5 wt % salt.

E. The hair conditioner composition of Paragraphs A-D, wherein the composition comprises from about 0.1 wt % to about 0.5 wt % salt, and preferably from about 0.2 wt % to about 0.4 wt % salt.

F. The hair conditioner composition of Paragraphs A-E, wherein the salt comprises sodium benzoate.

G. The hair conditioner composition of Paragraphs A-F, comprising less than 6.75 wt % BAPDMA, preferably less than about 6.50 wt % BAPDMA, and more preferably less than about 6.25 wt % BAPDMA.

H. The hair conditioner composition of Paragraphs A-G, comprising from about 2 wt % to about 6.7 wt % BAPDMA, preferably from about 2.2 wt % to about 6.5 wt % BAPDMA, more preferably from about 2.5 wt % to about 6.25 wt % BAPDMA, even more preferably from about 2.75 wt % to about 6 wt % BAPDMA.

I. The hair conditioner composition of Paragraphs A-H, wherein the fatty alcohol is selected from the group consisting of stearyl alcohol, brassical alcohol, cetyl alcohol, and combinations thereof.

J. The hair conditioner composition of Paragraphs A-I, comprising less than 8 wt % fatty alcohol, preferably less than 7.5 wt % fatty alcohol, more preferably less than 7 wt % fatty alcohol.

K. The hair conditioner composition of Paragraphs A-J, comprising from about 2.5 wt % to about 9 wt % fatty alcohol, preferably from about 3 wt % to about 8 wt % fatty alcohol, more preferably from about 3.25 wt % to about 7.5 wt % fatty alcohol, even more preferably from about 3.5 wt % to about 7 wt % fatty alcohol, and even more preferably from about 4 wt % to about 6.7 wt % fatty alcohol.

L. The hair conditioner composition of Paragraphs A-K, comprising a total gel network (GN) content (BAPDMA+fatty alcohol(s) (FAOH)) of from about 0.1 to about 0.6 molar, preferably from about 0.2 to about 0.5 molar, more preferably from about 0.3 to about 0.4 molar.

M. The hair conditioner composition of Paragraphs A-L, wherein the fatty alcohol comprises stearyl alcohol and the composition comprises a molar ratio of stearyl alcohol (C18 fatty alcohol) to total FAOH of from about 1:10 to about 1:1, preferably from about 1:5 to about 9:10, more preferably from about 3:10 to about 4:5, and most preferably from about 2:5 to about 7:10.

N. The hair conditioner composition of Paragraphs A-M, comprising a molar ratio of acid to BAPDMA of from about 1:2 to about 7:4, preferably from about 3:5 to about 1:2, more preferably from about 7:10 to about 5:4, and even more preferably from about 4:5 to about 1.3:1.

O. The hair conditioner composition of Paragraphs A-N, comprising a shear stress from about 50 Pa to about 600 Pa, preferably from about 75 Pa to about 575 Pa, more preferably about 100 Pa to about 565 Pa, even more preferably from about 105 Pa to about 550 Pa, and even more preferably from about 125 Pa to about 450 Pa, as measured by the Shear Stress Test Method, described herein.

P. The hair conditioner composition of Paragraphs A-O, wherein the composition is substantially free of or free of behentrimonium chloride, cetrimonium chloride, and/or stearamidopropyl dimethylamine.

Q. The hair conditioner composition of Paragraphs A-P, wherein the composition is substantially free of or free of mono long alkyl quaternized ammonium salts.

R. The hair conditioner composition of Paragraphs A-Q, wherein the composition is substantially free of, preferably free of an ingredient selected from the group consisting of silicone, propellants, phthalates, dyes, sulfates, formaldehyde donors, and combinations thereof.

S. The hair conditioner composition of Paragraphs A-R, wherein the conditioner composition comprises from about 40 wt % to about 99 wt % aqueous carrier, preferably from about 50 wt % to about 95 wt % aqueous carrier, more preferably from about 70 wt % to about 93 wt % aqueous carrier, and even more preferably from about 80 wt % to about 92 wt % aqueous carrier.

T. The hair conditioner composition of Paragraphs A-S, wherein the aqueous carrier comprises water.

U. The conditioner composition of Paragraphs A-T, comprising a pH from about 2.5 to about 5, preferably from about 3.5 to about 4.5, as measured according to the pH Test Method, described herein.

V. The conditioner composition of Paragraphs A-U, wherein the d-spacing is less than 30 nm and preferably less than 28 nm, according to the d-spacing (Lβ-basal spacing) of Lamella Gel Network Test Method, described herein.

W. The conditioner composition of Paragraphs A-V, wherein the d-spacing is from about 10 nm to about 32 nm, preferably from about 15 nm to about 30 nm, more preferably from about 17 nm to about 29 nm, even more preferably from about 18 nm to about 28 nm, and even more preferably from about 20 nm to about 27 nm, according to the d-spacing (Lβ-spacing) of Lamella Gel Network Test Method, described herein.

X. The conditioner composition of Paragraphs A-W, wherein the conditioner composition and/or the gel network comprises one peak, as measured according to the Differential Scanning calorimetry Test Method, described herein.

Y. The hair conditioner composition of Paragraphs A-X, further comprising a preservation system comprising:
   a. the salt wherein the salt comprises sodium benzoate;
   b. a second preservative selected from the group consisting of glycol, glyceryl ester, and combinations thereof;
   wherein the conditioner composition comprises a gel network.

Z. The hair conditioner composition of Paragraph Y, wherein the conditioner composition comprises from about 0.2 wt % to about 1.5 wt % preservation system, preferably from about 0.4 wt % to about 1 wt % preservation system, more preferably from 0.5 wt % to about 0.8 wt % preservation system, and even more preferably from about 0.6 wt % to about 0.8 wt % preservation system.

AA. The hair conditioner composition of Paragraphs Y-Z, wherein the preservation system comprises from about 20% to about 50% sodium benzoate, by weight of the preservation system, preferably from about 25% to about 50% sodium benzoate, by weight of the preservation system, more preferably about 30% to about 50% sodium benzoate, by weight of the preservation system, and even more preferably from about 30% to about 40% sodium benzoate, by weight of the preservation system.

BB. The hair conditioner composition of Paragraphs Y-AA, wherein the preservation system comprises from about 0.3 wt % to about 1.5 wt % of a second composition, preferably from about 0.32 wt % to about 1 wt % of a second composition, more preferably from about 0.33 wt % to about 0.8 wt % of a second composition, even more preferably from about 0.34 wt % to about 0.6 wt % of a second composition, even more preferably from about 0.35 wt % to about 0.5 wt % of a second composition, even more preferably from about 0.37 wt % to about 0.45 wt % of a second composition, and even more preferably from about 0.38 wt % to about 0.43 wt % of a second composition.

CC. The hair conditioner composition of Paragraphs Y-BB, wherein the preservation system comprises from about 50% to about 80% of the second composition, by weight of the preservation system, preferably from about 50% to about 75% of the second composition, by weight of the preservation system, more preferably from about 50% to about 70% of the second composition, by weight of the preservation system, and even more preferably from about 50% to about 67%, by weight of the preservation system.

DD. The hair conditioner composition of Paragraphs Y-CC, wherein the second composition comprises glycol selected from the group consisting of butylene, glycol, pentylene glycol, hexylene glycol, 1,2-hexanediol, caprylyl glycol, decylene glycol, and mixtures thereof.

EE. The hair conditioner composition of Paragraphs Y-DD, wherein the glycol comprises caprylyl glycol.

FE The hair conditioner composition of Paragraphs Y-EE, wherein the second preservative comprises glyceryl ester selected from the group consisting of glyceryl caprylate, glyceryl caprate, glyceryl undecylenate and mixtures thereof.

GG. The hair conditioner composition of Paragraphs Y-FF, wherein the preservation system comprises a weight ratio of sodium benzoate to the second composition from about 1:4 to about 1:1, preferably from about 1:3 to about 1:1, more preferably from about 1:2 to about 1:1, and even more preferably from about 1:1.7 to about 1:1.

HH. The hair conditioner composition of Paragraphs Y-GG, wherein the level of microbes is undetectable at two days, as measured according to the Bacterial and Fungal Microbial Susceptibility Test Methods, described herein.

II. The hair conditioner composition of Paragraphs Y-HH, wherein the composition is substantially free of, preferably free of a preservative ingredient selected from the group consisting of isothiazolinones including 5-chloro-2-methyl-4-isothiazolin-3-one and 2-methyl-4-isothiazolin-3-one (commercially available as Kathon™ CG from Dow®), benzyl alcohol, phenoxyethanol, cyclohexylglycerin, parabens, and combinations thereof.

JJ. The hair conditioner composition of Paragraphs Y-II wherein the composition is substantially free of, preferably free of ethylenediaminetetraacetic acid (EDTA) and salts thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioner composition comprising:
   a. an aqueous carrier;
   b. a single surfactant, wherein the single surfactant is behenamidopropyl dimethylamine and is present in the conditioner composition in an amount of about 2.5 wt % to about 6.7 wt %;
   c. about 3 wt % to about 8 wt % of a fatty alcohol;
   d. 0.05% to 0.4% of a salt selected from the group consisting of sodium benzoate, sodium salicylate, sodium chloride, sodium carbonate, sodium borate, sodium acetate, sodium citrate, potassium benzoate, potassium acetate, calcium gluconate, calcium chloride, potassium sorbate, and combinations thereof, and 0.38% to 0.43% of a second composition selected from the group consisting of glycol, glyceryl ester, and combinations thereof;
   wherein the molar ratio of behenamidopropyl dimethylamine to fatty alcohol is about 9:50 to about 2:3;
   wherein the composition comprises a uniform gel network;
   wherein the composition comprises d-spacing of less than 32 nm, as measured according to the d-spacing (Lβ-basal spacing) of Lamella Gel Network Test Method.

2. The composition of claim 1, wherein the fatty alcohol is selected from the group consisting of stearyl alcohol, brassica alcohol, cetyl alcohol, and combinations thereof.

3. The composition of claim 1, further comprising about 0.25 wt % to about 6 wt % of an acid selected from the group consisting of l-glutamic acid, lactic acid, hydrochloric acid, malic acid, succinic acid, acetic acid, fumaric acid, tartaric acid, citric acid, l-glutamic hydrochloride, maleic acid, and mixtures thereof.

4. The composition of claim 1, wherein the gel network content is about 0.2 to about 0.5 molar.

5. The composition of claim 1, comprising a shear stress of about 75 Pa to about 575 Pa.

6. The hair conditioner composition of claim 1, wherein the composition is substantially free of behentrimonium chloride, cetrimonium chloride, and/or stearamidopropyl dimethylamine.

7. The hair conditioner composition of claim 1, wherein the composition is substantially free of or free of mono long alkyl quaternized ammonium salts.

8. The hair conditioner composition of claim 1, wherein the composition is substantially free of an ingredient selected from the group consisting of silicone, propellants, phthalates, dyes, sulfates, formaldehyde donors, and combinations thereof.

9. The conditioner composition of claim 1, comprising a pH of about 2.5 to about 5, as measured according to the pH Test Method.

10. The conditioner composition of claim 1, wherein the conditioner composition comprises one peak, as measured according to the Differential Scanning Calorimetry Test Method.

11. A hair conditioner composition comprising:
   a. an aqueous carrier;
   b. a single surfactant, wherein the single surfactant is behenamidopropyl dimethylamine and is present in the conditioner composition in an amount of about 2.5 wt % to about 6.25 wt %;
   c. a fatty alcohol selected from the group consisting of stearyl alcohol, brassica alcohol, cetyl alcohol, and combinations thereof;
   d. a preservation system comprising
      i. 0.05% to 0.4% sodium benzoate, by weight of the composition;
      ii. 0.38% to 0.43% of a second composition selected from the group consisting of glycol, glyceryl ester, and combinations thereof;
      wherein the molar ratio of sodium benzoate to the second composition is about 1:4 to about 1:1;
   wherein the molar ratio of behenamidopropyl dimethylamine to fatty alcohol is about 3:20 to about 3:4;
   wherein the composition comprises a uniform gel network;
   wherein the composition comprises d-spacing of about 15 nm to about 30 nm, as measured according to the d-spacing (Lβ-basal spacing) of Lamella Gel Network Test Method.

12. The conditioner composition of claim 11, wherein the d-spacing is about 20 nm to about 27 nm, according to the d-spacing (Lβ-basal spacing) of Lamella Gel Network Test Method.

13. The composition of claim 11, wherein the gel network content is greater than 0.3 molar.

14. The hair conditioner composition of claim 11, wherein the second composition comprises glycol selected from the group consisting of butylene glycol, pentylene glycol, hexylene glycol, 1,2-hexanediol, caprylyl glycol, decylene glycol, and mixtures thereof.

15. The hair conditioner composition of claim 14, wherein the glycol comprises caprylyl glycol.

16. The hair conditioner composition of claim 11, wherein the preservation system's second composition comprises glyceryl ester selected from the group consisting of glyceryl caprylate, glyceryl caprate, glyceryl undecylenate and mixtures thereof.

17. The hair conditioner composition of claim 11, wherein the preservation system comprises about 0.2% to about 0.4% of the sodium benzoate, by weight of the composition.

18. The hair conditioner composition of claim 11, wherein the level of microbes is undetectable at two days, as measured according to the Bacterial and Fungal Microbial Susceptibility Test Methods.

19. The hair conditioner composition of claim 11, wherein the preservation system is substantially free of a preservative ingredient selected from the group consisting of ethylenediaminetetraacetic acid and salts thereof, isothiazolinones, benzyl alcohol, phenoxyethanol, cyclohexylglycerin, parabens, and combinations thereof.

* * * * *